(12) United States Patent
Allen et al.

(10) Patent No.: US 9,827,083 B2
(45) Date of Patent: Nov. 28, 2017

(54) PELVIC IMPLANT SYSTEM AND METHOD

(75) Inventors: John J. Allen, Mendota Heights, MN (US); James R. Mujwid, Crystal, MN (US); Kevin R. Arnal, Excelsior, MN (US); Jessica E. Felton, Minneapolis, MN (US); David J. Sogard, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 34 days.

(21) Appl. No.: 13/568,093

(22) Filed: Aug. 6, 2012

(65) Prior Publication Data
US 2013/0204075 A1    Aug. 8, 2013

Related U.S. Application Data

(60) Provisional application No. 61/515,180, filed on Aug. 4, 2011, provisional application No. 61/545,104, filed on Oct. 7, 2011, provisional application No. 61/547,467, filed on Oct. 14, 2011, provisional application No. 61/547,503, filed on Oct. 14, 2011, provisional application No. 61/607,332, filed on Mar. 6, 2012, provisional application No. 61/607,891, filed on Mar. 7, 2012, provisional application No. 61/608,436, filed on Mar. 8, 2012, provisional application No. 61/608,478, filed on Mar. 8, 2012, provisional application No. 61/653,199, filed on May
(Continued)

(51) Int. Cl.
*A61F 2/00*    (2006.01)
*A61B 17/04*   (2006.01)
*A61B 17/34*   (2006.01)
*A61B 17/00*   (2006.01)
*A61B 17/06*   (2006.01)

(52) U.S. Cl.
CPC ........ *A61F 2/0045* (2013.01); *A61B 17/0401* (2013.01); *A61B 17/3468* (2013.01); *A61F 2/0036* (2013.01); *A61B 2017/00805* (2013.01); *A61B 2017/00867* (2013.01); *A61B 2017/0409* (2013.01); *A61B 2017/0412* (2013.01); *A61B 2017/0417* (2013.01); *A61B 2017/0464* (2013.01); *A61B 2017/0496* (2013.01); *A61B 2017/06052* (2013.01); *A61B 2017/06176* (2013.01); *A61F 2210/0014* (2013.01); *A61F 2220/0016* (2013.01)

(58) Field of Classification Search
CPC ...... A61B 2017/00805; A61B 17/0401; A61B 2017/0412; A61B 2017/0464; A61B 2017/06052; A61B 2017/0414; A61B 2017/0437
USPC ................................. 600/37, 29–31
See application file for complete search history.

(56) References Cited

U.S. PATENT DOCUMENTS 5,520,606 A * 5/1996 Schoolman et al. ............ 600/31
2002/0143234 A1* 10/2002 LoVuolo ........................ 600/30
(Continued)

*Primary Examiner* — Christine H Matthews
*Assistant Examiner* — Joshua D Lannu
(74) *Attorney, Agent, or Firm* — Brake Hughes Bellermann LLP

(57) ABSTRACT

Systems and methods are provided and adapted to engage and pull (e.g., pull up) or reposition urethral support tissue, such as the portion of the perineal membrane above or below the urethra. The perineal membrane intersects the urethra and vagina at the midurethra or distal location and can thus be stabilized or controlled in a manner that helps restore continence.

13 Claims, 26 Drawing Sheets

Related U.S. Application Data

30, 2012, provisional application No. 61/653,213, filed on May 30, 2012, provisional application No. 61/653,224, filed on May 30, 2012, provisional application No. 61/653,236, filed on May 30, 2012.

(56)  References Cited

U.S. PATENT DOCUMENTS

| | | | |
|---|---|---|---|
| 2004/0106847 A1* | 6/2004 | Benderev | A61B 17/0401 600/37 |
| 2009/0222025 A1* | 9/2009 | Catanese et al. | 606/139 |
| 2010/0174134 A1* | 7/2010 | Anderson et al. | 600/37 |
| 2010/0197999 A1* | 8/2010 | Deegan et al. | 600/30 |
| 2010/0210897 A1* | 8/2010 | Arnal et al. | 600/30 |
| 2010/0331612 A1* | 12/2010 | Lashinski et al. | 600/37 |
| 2011/0082328 A1* | 4/2011 | Gozzi et al. | 600/30 |
| 2011/0230707 A1* | 9/2011 | Roll et al. | 600/37 |

\* cited by examiner

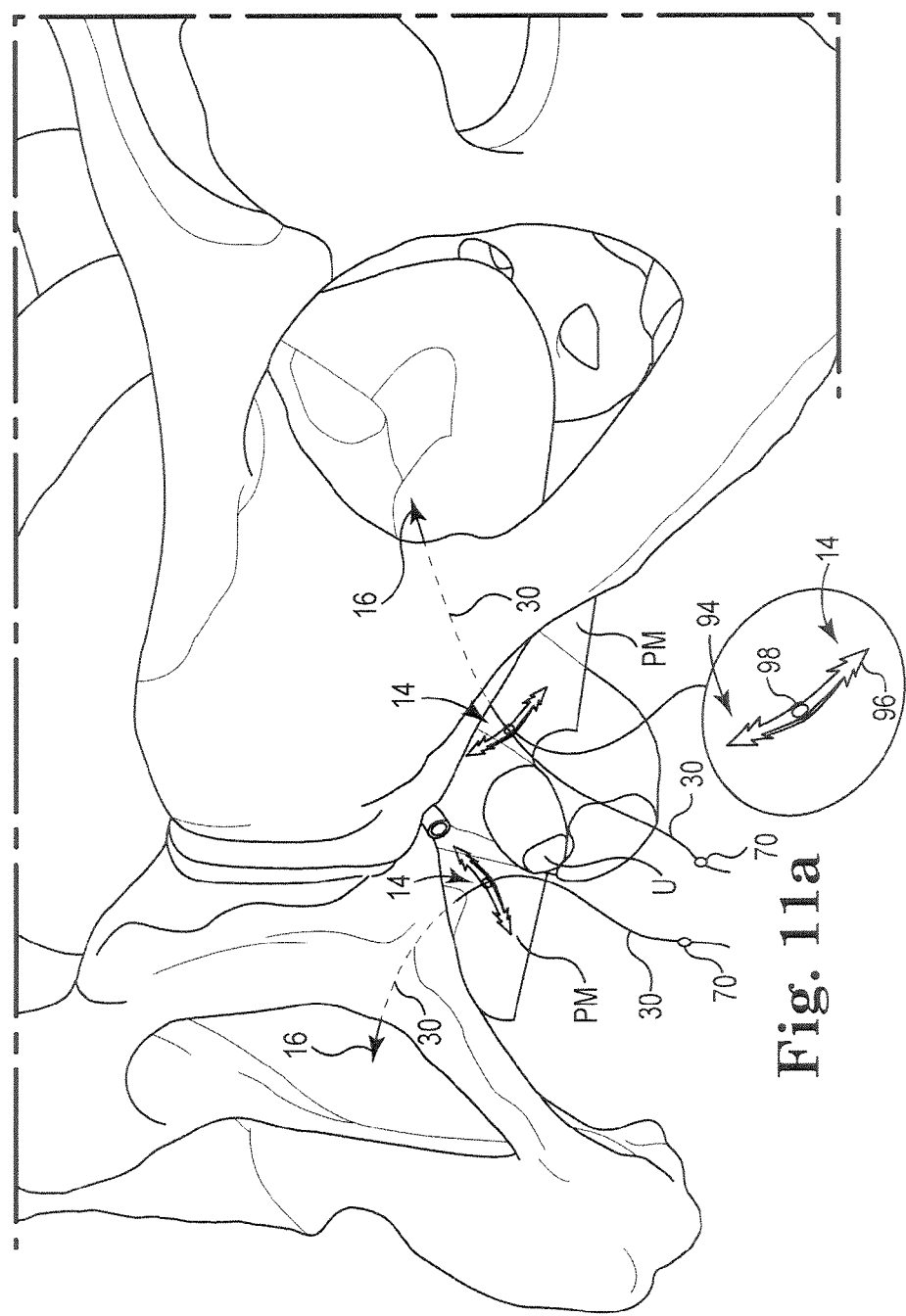

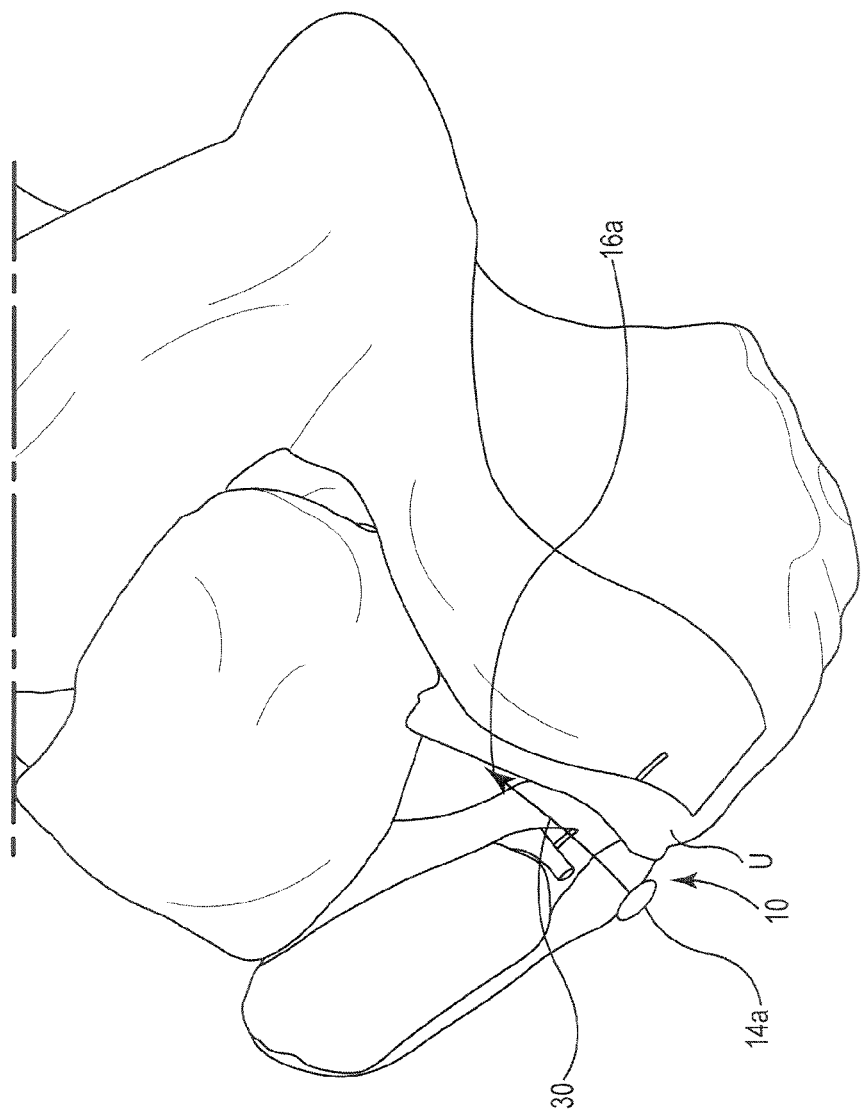

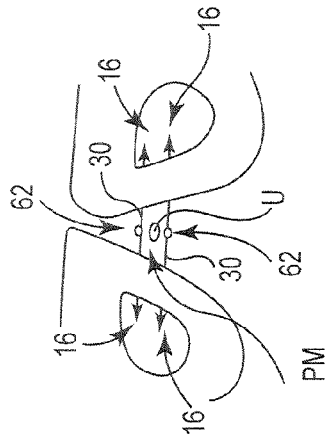
Fig. 17
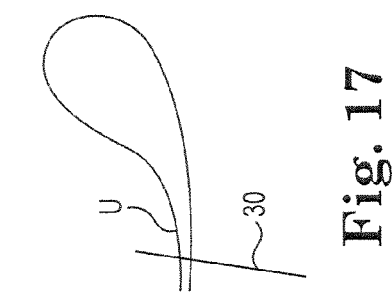
Fig. 18
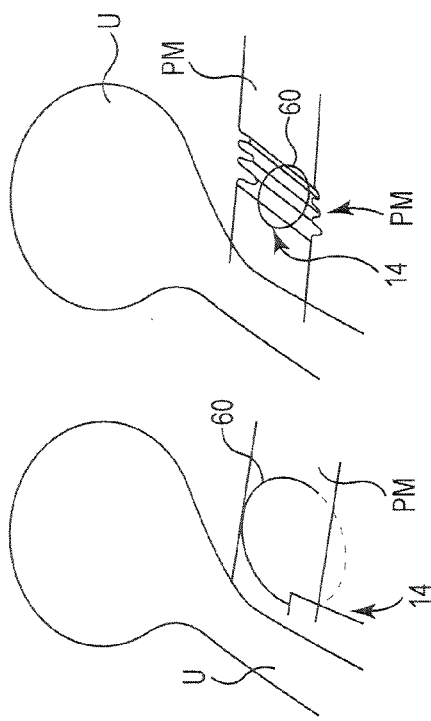
Fig. 15
Fig. 16
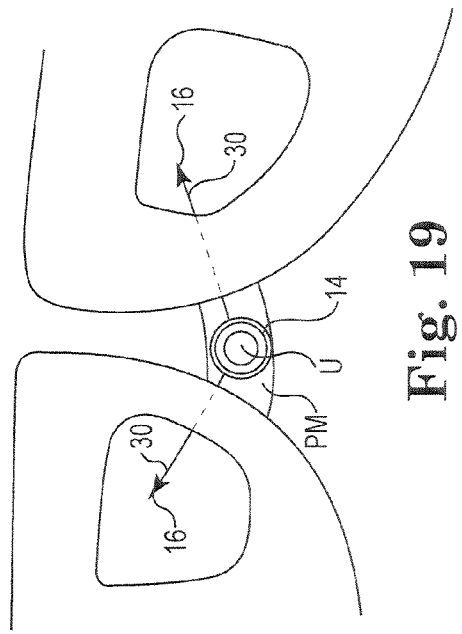
Fig. 19

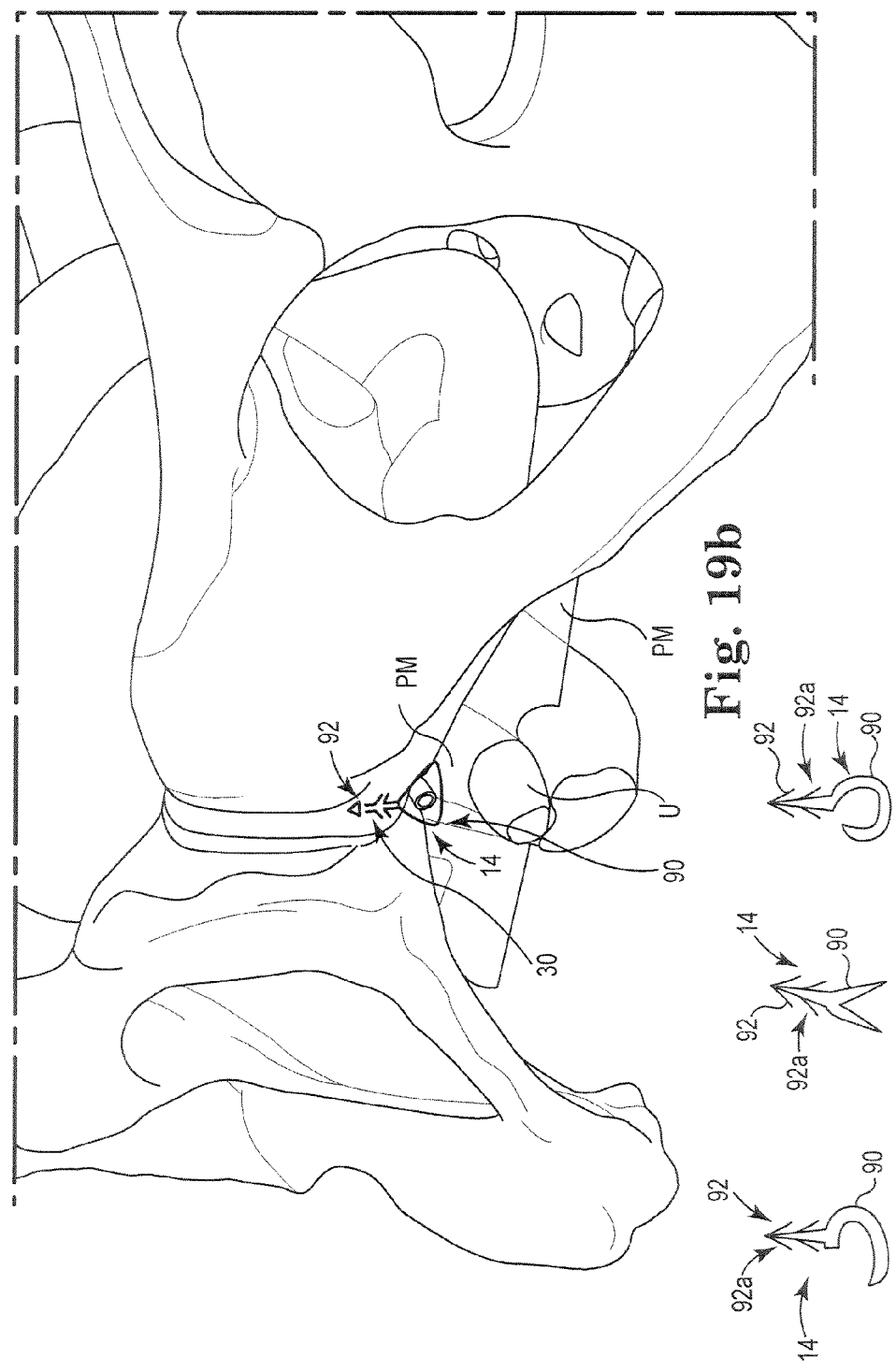

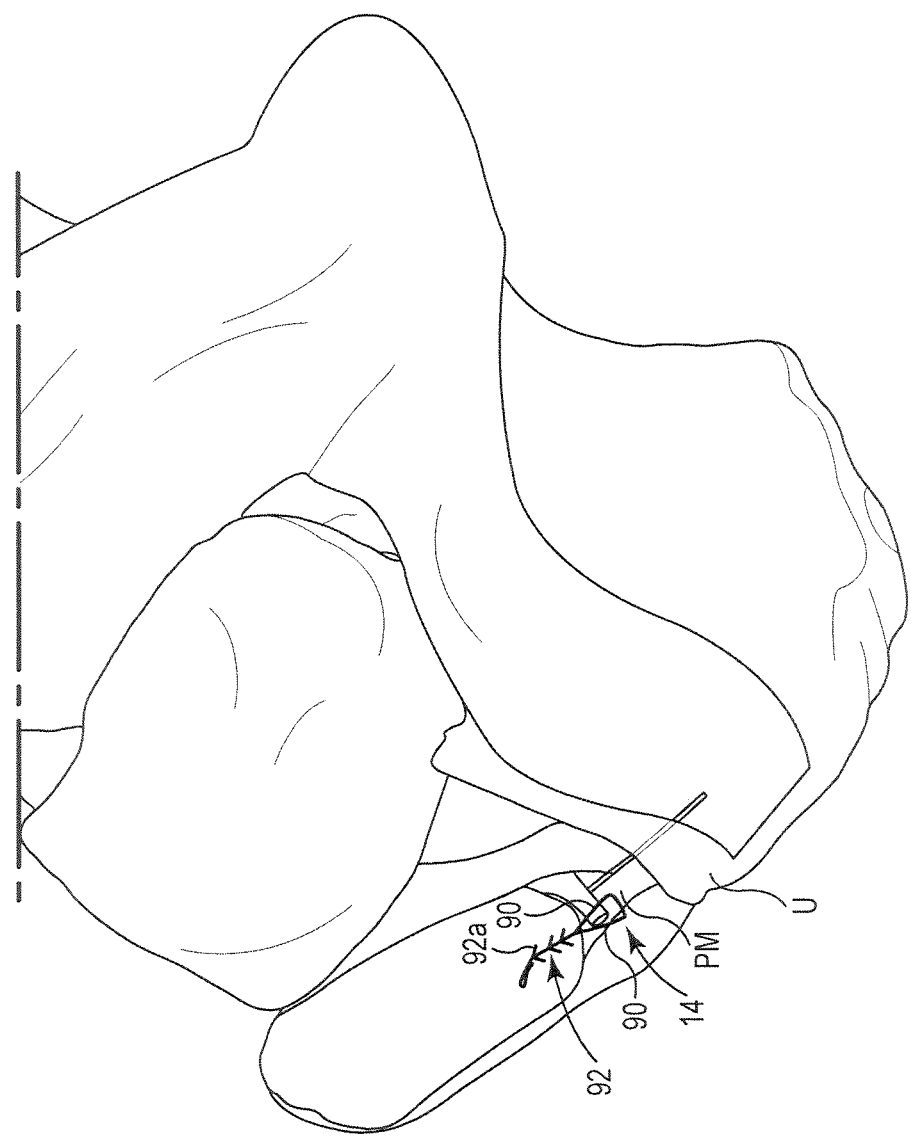

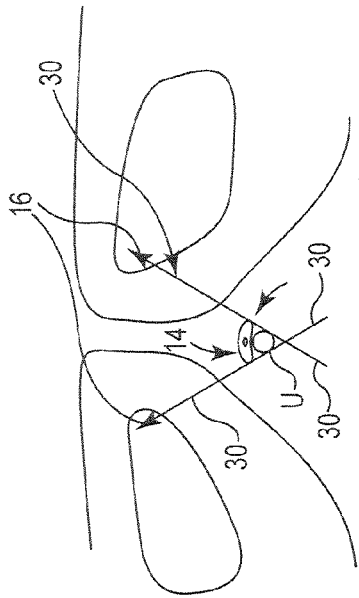
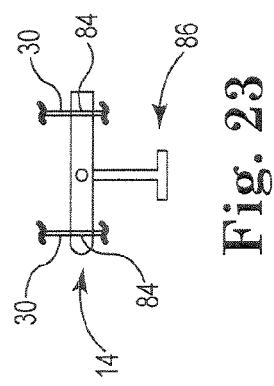
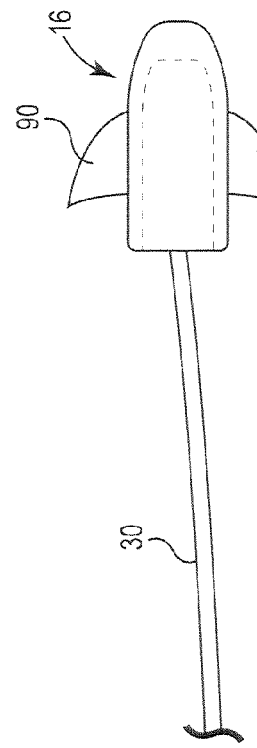

PELVIC IMPLANT SYSTEM AND METHOD

PRIORITY

This application claims priority to and the benefit of U.S. Provisional Patent Application No. 61/515,180, filed Aug. 4, 2011, U.S. Provisional Patent Application No. 61/545,104, filed Oct. 7, 2011, U.S. Provisional Patent Application No. 61/547,467, filed Oct. 14, 2011, U.S. Provisional Patent Application No. 61/547,503, filed Oct. 14, 2011, U.S. Provisional Patent Application No. 61/607,332, filed Mar. 6, 2012, U.S. Provisional Patent Application No. 61/607,891, filed Mar. 7, 2012, U.S. Provisional Patent Application No. 61/608,436, filed Mar. 8, 2012, U.S. Provisional Patent Application No. 61/608,478, filed Mar. 8, 2012, U.S. Provisional Patent Application No. 61/653,199, filed May 30, 2012, U.S. Provisional Patent Application No. 61/653,213, filed May 30, 2012, U.S. Provisional Patent Application No. 61/653,224, filed May 30, 2012, U.S. Provisional Patent Application No. 61/653,236, filed May 30, 2012; with each of the above-referenced applications and disclosures fully incorporated herein by reference in their entirety.

FIELD OF THE INVENTION

The present invention relates to apparatus, tools and methods for treating pelvic conditions and, more particularly, systems and methods to support pelvic tissue by acting on, stabilizing, positioning or controlling the position of the perineal membrane or like anatomical structures.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. The urethra is the tube that passes urine from the bladder out of the body. The narrow, internal opening of the urethra within the bladder is the bladder neck. In this region, the bladder's bundled muscular fibers transition into a sphincteric striated muscle called the internal sphincter. The urethra extends from the bladder neck to the end of the penis. The male urethra is composed of three portions: the prostatic, bulbar and pendulus portions. The prostatic portion is the widest part of the tube, which passes through the prostate gland. The rectum is the most distal portion of the gastrointestinal tract. The exterior opening of the rectum is the anus. Fecal continence is related to control of the exterior sphincter and interior sphincter of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder," "frequency/urgency syndrome," or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. Midurethral slings have been effective. One type of procedure, found to be an especially successful treatment option for SUI in both men and women, is a sling and support procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension structures or sutures to a point of attachment (e.g., tissue or bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534, 6,110,101, 6,911,003, 6,652,450, and International PCT Publication No. 2008/057261, all of which are herein incorporated by reference in their entirety. Further, U.S. patent application Ser. No. 13/556,167, filed Jul. 23, 2012 and entitled "Pelvic Implant System and Method" is fully incorporated by reference herein in its entirety.

Fecal incontinence, like urinary incontinence, has proven to be challenging to treat. Patients whose fecal incontinence is caused by external anal sphincter injury is treated surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic gracioplasty, artificial sphincter procedures, and sacral nerve stimulation. Success has been limited, and the various treatment modalities can result in morbidity.

There is a desire for a minimally invasive yet highly effective treatment modality that can be used with minimal to no side effects for the treatment of both urinary and fecal incontinence. Such a modality should reduce the complexity of a treatment procedure, be biocompatible, should reduce pain, operative risks, infections and post operative hospital stays, and have a good duration of activity. Further, the method of treatment should also improve the quality of life for patients.

SUMMARY OF THE INVENTION

The present invention can include surgical instruments, implantable articles, and methods for urological applications, particularly for the treatment of stress and/or urge urinary incontinence, fecal incontinence, and prolapse by implanting a constraining device. The constraining device or implant can control and eliminate rotation of the urethra that is associated with incontinence.

Embodiments of the present invention can include apparatus and methods for treating urinary incontinence, fecal incontinence, and other pelvic defects or dysfunctions, in both males and females using one or more implants to reinforce the supportive tissue of the urethra. The implants are configured to engage and pull (e.g., pull up or down) or reposition the supportive tissue, such as the perineal membrane. The perineal membrane is the fibrous membrane in the perineum that intersects the urethra and vagina near the midurethra location and can thus be stabilized or controlled in a manner that helps restore continence. As such, systems, methods and implants can be utilized to eliminate the need for mesh or other supportive structures directly engaging under the urethra that is common with other incontinence slings. The implants can be shaped to facilitate such support, e.g., provided with anchoring end portions, barbs or other devices of many available shapes and configurations. One or more anchors or tissue engagement portions can be employed to attach and stabilize the implants or devices to tissue.

Embodiments of the present invention can provide smaller implants or devices, fewer implant or device components, thus reducing the size and number of incisions, improving implant manipulation and adjustment, the complexity of the insertion and deployment steps, and healing times.

The implants can resist movement of tissue such as, for example, forward rotational movement of the urethra or surrounding tissue. The present implant embodiments can utilize a perineal incision or puncture and a paraurethral constraining device. Alternatively, the device may be implanted transvaginally.

In certain embodiments, one or more medial support devices are provided at the perineal membrane, above or below the urethra. For instance, supraurethral or suburethral suspension elements are provided for the treatment of SUI and other disorders. The support, extension or suspension elements can apply mechanical traction to the urethra in a manner similar to a mini-sling device, wherein tension is applied at the midurethral position to lift and support that anatomical structure during stress events, such as coughing or physical activity.

A device or portion, such as a medial or proximal anchor, is fixed above or below the urethra that is known to have relatively high strength and toughness. Such anatomical structures can include the uterovaginal fascia, endopelvic fascia, perineal membrane or other anatomical features at which connective support of the urethra can be established. The medial anchor can include a self-expanding anchor, mesh, an elongated member, a plate, a tube, a "toggle" anchor, which is a small or elongated structure that can be placed through the tissue via a small puncture or like incision and then rotates after deployment so that it cannot back out through the incision hole, or a myriad of other anchoring and tissue engagement devices.

A second or distal device, such as a distal anchor or engagement device, can be placed in a lateral or superior position such that a connection between the medial and lateral distal devices (via a suture, mesh, wire or like connection) can provide tensile support for the urethra during stress events. The distal anchor device can be fixated to, or around, the tendinous arch of the levator ani (white line), the Cooper's ligament, the obturator foramen, obturator internus, abdominal fascia, sacrospinous ligament, prepubic fascia or muscle, the pubic symphysis cartilage, or other stable anatomical structures. The distal anchor devices can include a body portion, a beveled tip, one or more expandable barbs, a thru-aperture, and an opposing end. The suture or like extension member can be adapted to string or thread through the respective apertures of a series or array of such distal anchors.

The medial device can spread or better distribute the tension load over a larger surface compared to a thin edge surface. This, in turn, promotes stability of the implant and connecting suture and, ultimately, the target support tissue.

Various procedural steps or methods can be implemented to deploy and anchor the implant of the present invention. In one embodiment, the medial device is implanted, a needle is withdrawn, a free suture or connector end is delivered through the insertion opening, one or more distal anchors are delivered and implanted, and the connecting suture is properly tensioned between the anchors to provide proper support. The suture or other support extensions members can be constructed to be generally flexible, or can have limited elasticity—e.g., bungee-type attributes.

Various anchoring systems, devices, techniques and placement locations are provided to facilitate the support and rotational prevention of exemplary embodiments, as well as hingable anchor constructs and configurations, as well as suture pathways and anchoring positions.

BRIEF DESCRIPTION OF THE DRAWINGS

FIG. 11-11b is a schematic view of medial devices engaged with the perineal membrane, in accordance with embodiments of the present invention.

FIG. 12 is a schematic view of a medial device engaged at or below the skin surface, and distal anchoring, in accordance with embodiments of the present invention.

FIGS. 15-16 are schematic views of a tissue bunching implant adapted for engagement with the perineal membrane, in accordance with embodiments of the present invention.

FIGS. 17-18 are schematic views of a perineal membrane buttressing implant system in accordance with embodiments of the present invention.

FIG. 23-24 are schematic views of a generally T-shaped medial device and anchoring support, in accordance with embodiments of the present invention.

FIG. 25 is a distal anchor device and suture, in accordance with embodiments of the present invention.

DETAILED DESCRIPTION OF PREFERRED EMBODIMENTS

Figure 1:
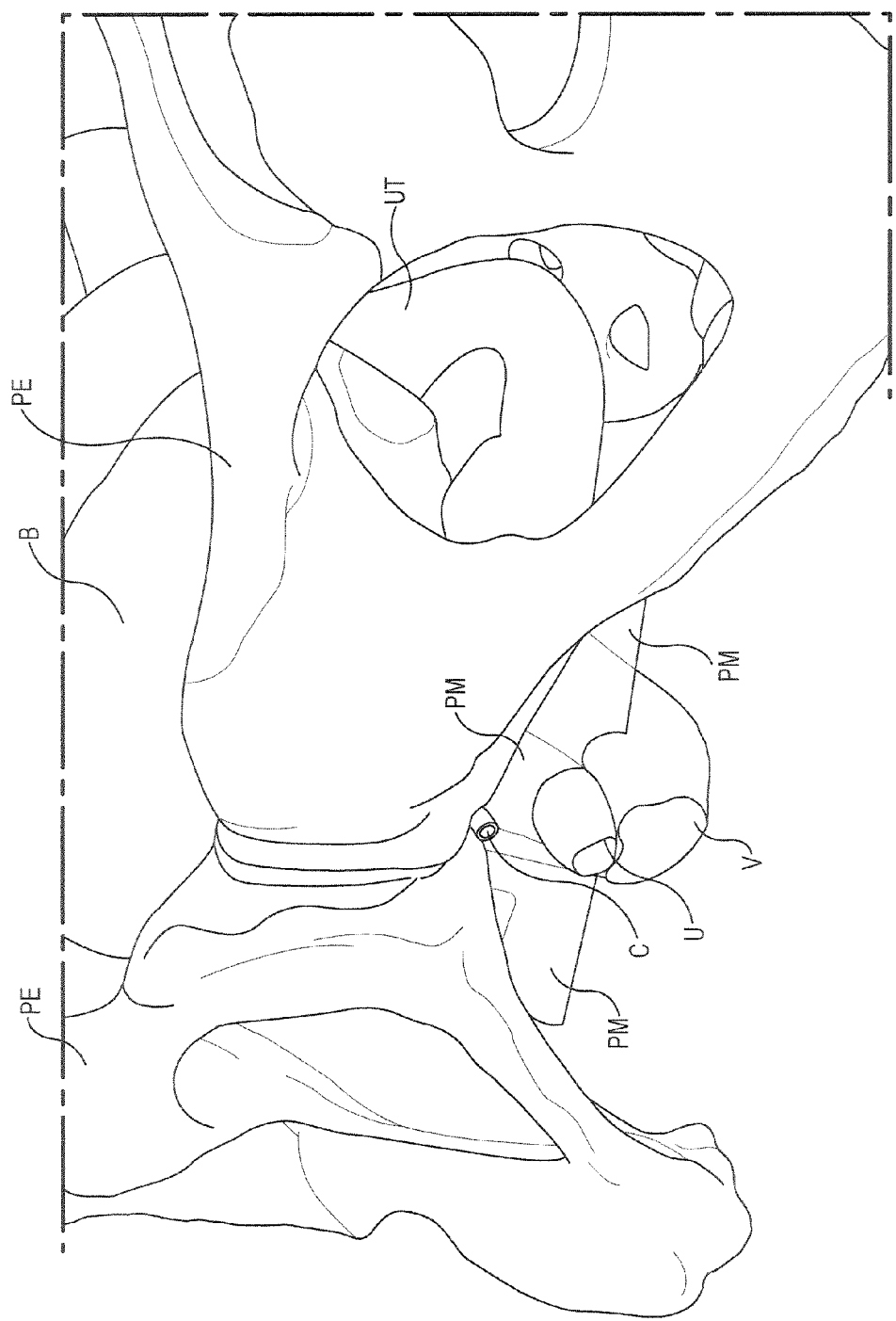
FIG. 1 is a schematic view of various anatomical structures of the female pelvic region, including urinary and reproductive systems.

FIG. 1 shows a schematic view of relevant portions of the female pelvic region, and the urinary and reproductive system, including the pelvis PE, vagina V, uterus UT, urethra U, bladder B and the deep clitoral vein C. Further, a portion of the perineal membrane PM is shown at the midurethra/distal location, providing a viable paraurethral target for stabilizing or controlling the position and movement of the urethra to assist in restoring continence.

Embodiments of the present invention can include apparatus and methods for treating urinary incontinence, fecal incontinence, and other pelvic defects or dysfunctions, in both males and females using one or more lateral implants to reinforce the supportive tissue of the urethra. One or more implant devices 10 are configured to engage and pull (e.g., pull up) or reposition support tissue (e.g., paraurethral), such as the perineal membrane, uterovaginal fascia, endopelvic fascia, or other anatomical features at which connective support of the urethra can be established. The perineal membrane intersects the urethra and vagina at the midurethra/distal location and can thus be stabilized or controlled in a manner that helps restore continence. As such, the implants 10 can be utilized to eliminate the need for mesh or other supportive structures under the urethra that is common with other incontinence slings. The implants can be shaped to facilitate such support, e.g., provided with anchoring end portions 12, barbs or other devices of many available shapes, sizes and configurations, and extension members 30.

Various embodiments of the extension members 30 can be constructed of a suture, a thin flat member, braided fibers, braided nano-fibers, an elongate mesh and other various materials and constructs. For those embodiments including braided nano-fibers, the extension member 30 can enhance and draw more collagen-producing cells to the material to promote tissue ingrowth and healing. The extension member 30 of certain embodiments of the present invention can be constructed to be generally flexible, or to have limited elasticity—e.g., bungee type attributes. For instance, the member 30 extending between one or more devices 14, 16 (e.g., anchors or other features) can be an elongate member constructed of an elastomeric material having desirable tensile properties. As such, the member 30 can be extended or stretched out for deployment and then released to provide desirable taut tension. The travel or stretching/rebound characteristics of the member 30 can vary depending on the particular elastomeric materials used in its construction. The extension member 30, such as a suture, can further include various extending tines or barbs to facilitate tissue traction and grabbing during and after deployment.

One or more opposing devices 14, 16 or tissue engagement or support portions can be employed to attach and stabilize the implants to the tissue, as well as provide selective adjustment. The device portions can be configured to engage, directly or indirectly, soft tissue and can include various barbs, tines, serrated edges, extending fibers, or other similar structural feature to promote tissue fixation. In various embodiments, one or more of the devices 14, 16 can include anchors that can be implanted in a direction lateral from the urethra, or above or below the urethra—e.g., supraurethral or suburethral. The anchors can generally be small enough to be unnoticeable by both the patient and the patient's sexual partner. The anchors and other devices and components of the system 10 may be constructed from various biocompatible materials, such as known polymers and metals that promote long-term resilience, or other materials known to those skilled in the art.

In various embodiments, the one or more implants 10 can be placed in strategically located positions to pull up or otherwise tighten tissue and/or muscle lateral or otherwise intersecting or attached (directly or indirectly) with the urethra to generally stabilize the anatomical structure of the patient. Various systems, devices, structures, techniques and methods, alone or in combination, as disclosed in U.S. Pat. Nos. 7,500,945, 7,407,480, 7,351,197, 7,347,812, 7,303,525, 7,025,063, 6,911,003, 6,691,711, 6,648,921, 6,612,977, 6,802,807, 2002/0161382, 2002/0147382, 2002/151762, 2004/0039453, 2008/0057261, 2008/0045782, 2010/0105979, 2011/0144417, and 2011/0201876 and International PCT Publication Nos. WO 2008/057261 and WO 2007/097994, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

Referring generally to FIGS. 2-23, various embodiments are shown of the tissue constraining or positioning implant system 10 having one or more attachment points in one or more membranes or other target tissue locations. Embodiments can function to restrict, limit or control movement of the mid or distal urethra, or surrounding tissue. Further, embodiments can assist in resisting forward rotational movement of the urethra or surrounding tissue, and can provide support and tension during events, such as coughing or physical activity. Various advantages of the implant 10 embodiments depicted herein include, frontal access and simpler anatomy to address, less vascularity and bleeding, reduced risk of creating retention and de novo urge, and the ability to test for continence before surgery. Additionally, the implants 10 can act to oppose rotational movement of the urethra, thereby eliminating or lessening the effects of stress urinary incontinence.

When direct midurethral support is implanted in the female patient, the midurethra is restrained from movement. However, the bladder neck can remain mobile and move downward during a stress event due to elevated abdominal pressure. The resulting effect is that the urethra can be kinked at the midurethra location, causing a closure of the urethra. Like kinking a garden hose, the flow of fluid can be restricted or prevented.

Certain of the devices of the implant 10, e.g., the lateral anchor 16, can be generally provided in a back-to-back serial configuration, with a suture or like extension member extending to provide adjustable support between the devices 14, 16. The device 14 can include one or more anchor or other medial or proximal devices. The device 16 can include one or more anchor or other second lateral or distal devices.

Certain embodiments of the medial device 14 can include structures adapted to attach to or span across a portion of the perineal membrane, or like tissue, to facilitate engagement, compression or anchoring with the tissue. For instance, a plate, mesh material, tissue cinching device, stent-like device, sling, ring, clip, coil, spring, strap, pad, patches, or similar structures, can be affixed to, directly or indirectly, the perineal membrane PM, with such devices or anchors 14 then being connected to the lateral anchor 16 via the extension member 30. These structures can be attached to tissue via sutures, anchors, and similar tissue engagement devices. The devices 14 and related structures can include rigid, semi-rigid, flexible, or shape memory polymer or metal materials. The anchoring vector from the device 14 to the one or more anchors 16 (e.g., via the member 30) can extend upward away from the urethra U, downward away from the urethra U, or generally lateral from the urethra U.

One-way locking devices 70 can be incorporated with any of the devices 14, 16, or along (e.g., thread along) the member 30 such that the physician can adjust the tensioning of the implant 10 to the desired level and fix the tension for optimal support and the promotion of continence.

Figure 2:
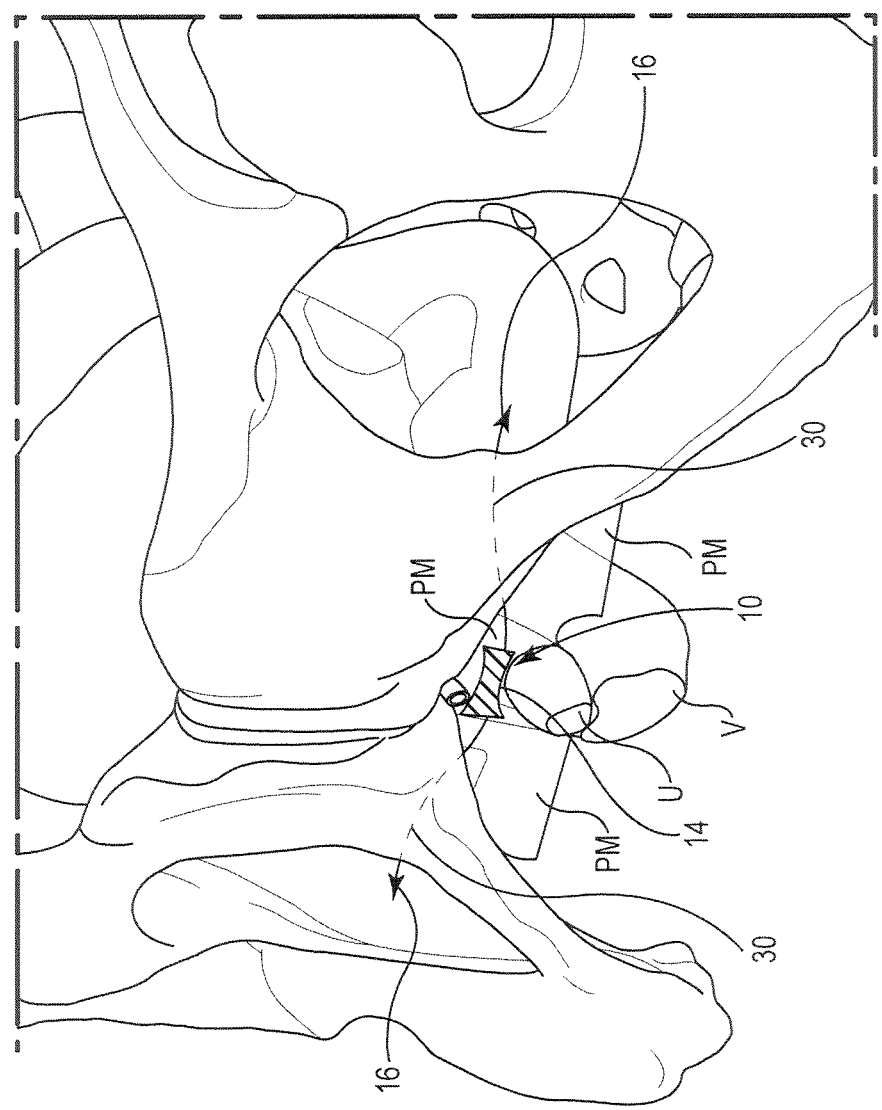
FIGS. 2-9 are schematic views of various anatomical structures of the female pelvic region, and implant devices having medial devices provided with the perineal membrane, and distal anchoring of the implant a distance away from the medial device, in accordance with embodiments of the present invention.

Referring to FIG. 2 various embodiments of the implant 10 can include the one or more medial devices 14, one or more extension members 30, and one or more anchor devices 16. The extension members 30 can extend from a terminus or other portion of the device 14. One or more of the anchors 16 may be operatively coupled to the distal ends of the extension members 30 to provide for engagement in the tissue. The implant 10 works to constrain the urethra U in a relatively fixed position. The length, width, and flexibility of the implant 10 may vary greatly depending on the particular procedure and placement of the device 14, 16. The device 14 can span across or attach to a portion of the perineal membrane PM above (e.g., supraurethral), or below (e.g., suburethral), the urethra U. However, unlike other sling or hammock-like implants, the implant 10 can adjust the support and positioning of the urethra U via attachment and adjustment to the perineal membrane PM rather than directly engaging the urethra U. The device 14 can be constructed of a flexible mesh or other known biocompatible polymer or material known by one skilled in the art.

The medial device 14 can be implanted between the skin and perineal membrane or other internal fascia. Once implanted, the device 14 can also facilitate the infiltration of tissue and cells to promote tissue in-growth and, in turn, fixation of the implant 10 to the surrounding anatomical structures. The device 14 may be suspended anterior to the urethra U.

The device or anchor 16 may be configured as a soft tissue anchor. The anchors 16 can have barbs, tines, serrated edges, extending fibers, or other similar structural feature to promote tissue engagement and stability. The anchors 16 can be implanted in a direction lateral from the urethra U. The anchors 16 can be small enough for percutaneous implantation such that they are unnoticeable by both the patient and his/her sexual partner. The anchors 16 can be constructed from various biocompatible materials, such as known polymers and metals that promote long-term resilience or other materials known to those skilled in the art. Further, multi-anchor or serial/array anchor configurations such as those disclosed herein can be employed as anchors 16 for any embodiment of the present invention.

A coupling mechanism, aperture, or like feature or construct can be provided to couple the device 14 to the members 30, or the anchor device 16. In exemplary embodiments, the extension member 30 can include a suture spanning between and attaching the devices 14, 16. These structures and configurations can provide adjustable tensioning for the implant 10. A myriad of attachment structures or techniques can be utilized to connect the ends of the one or more devices 14 to the device 16.

Figure 3:
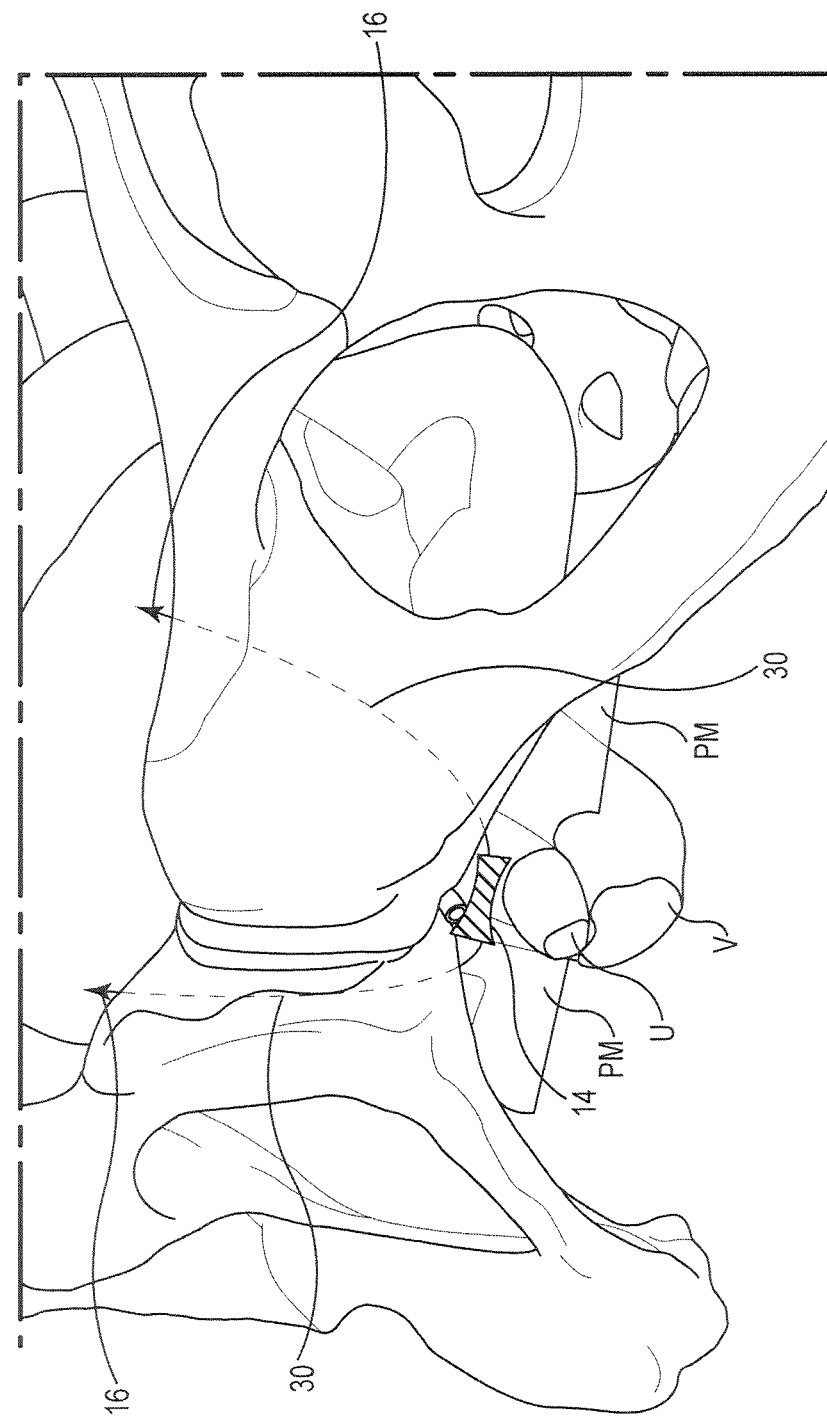
Figure 4:
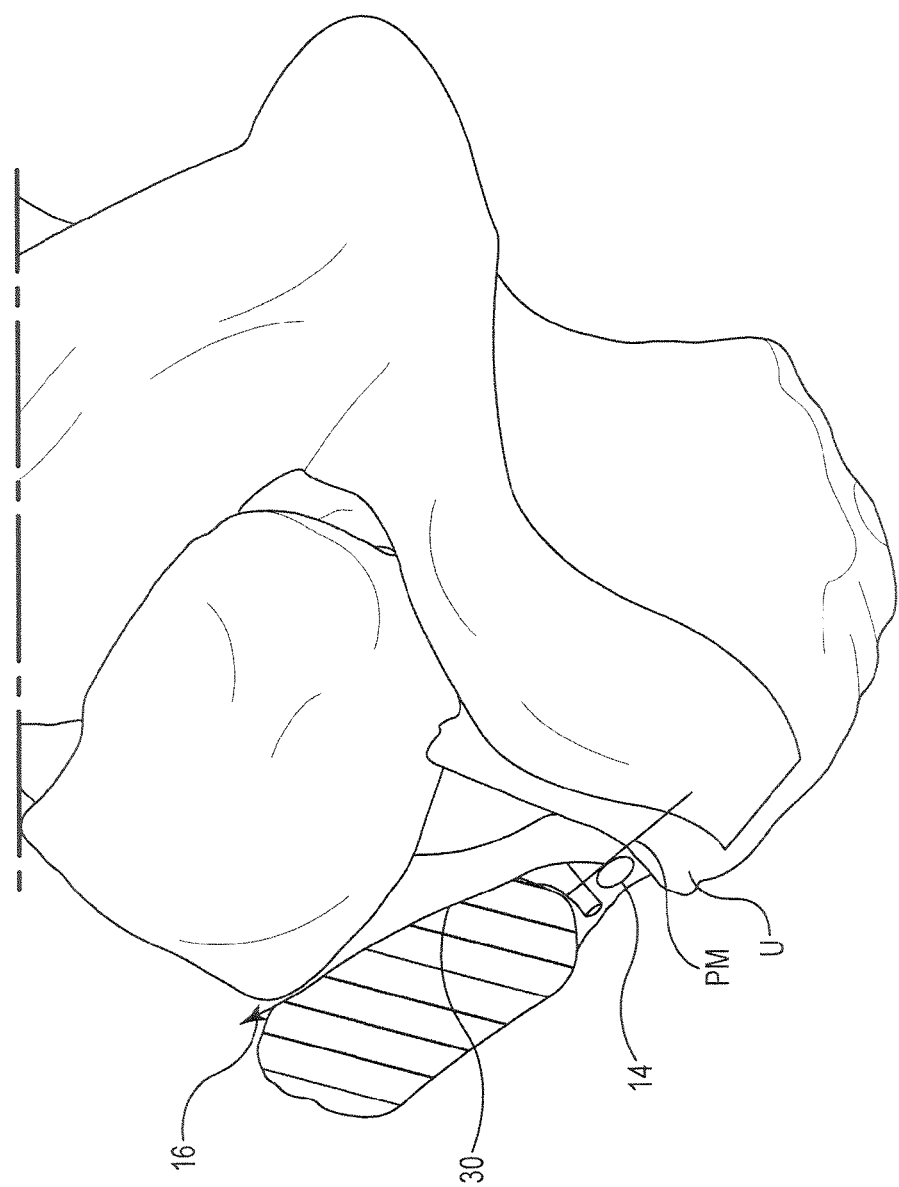
Figure 5:
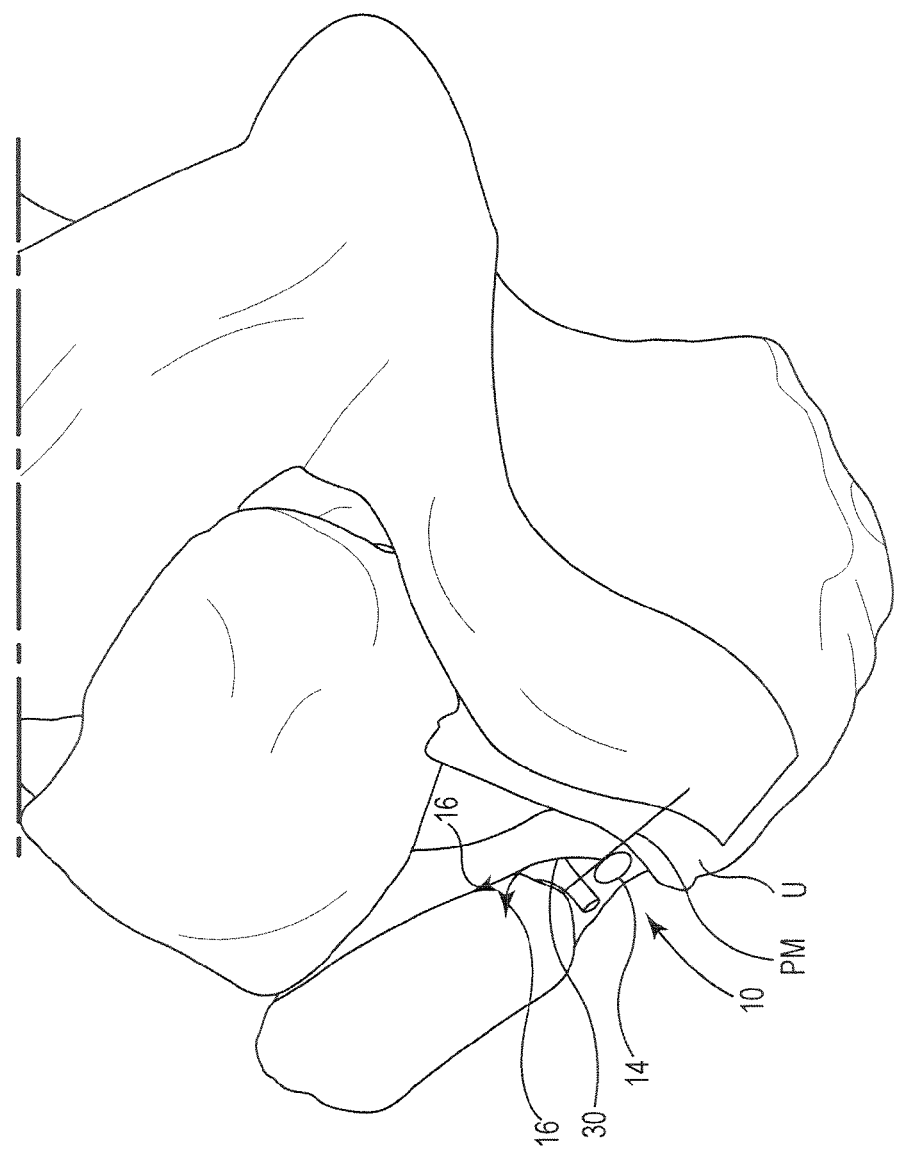
Figure 6:
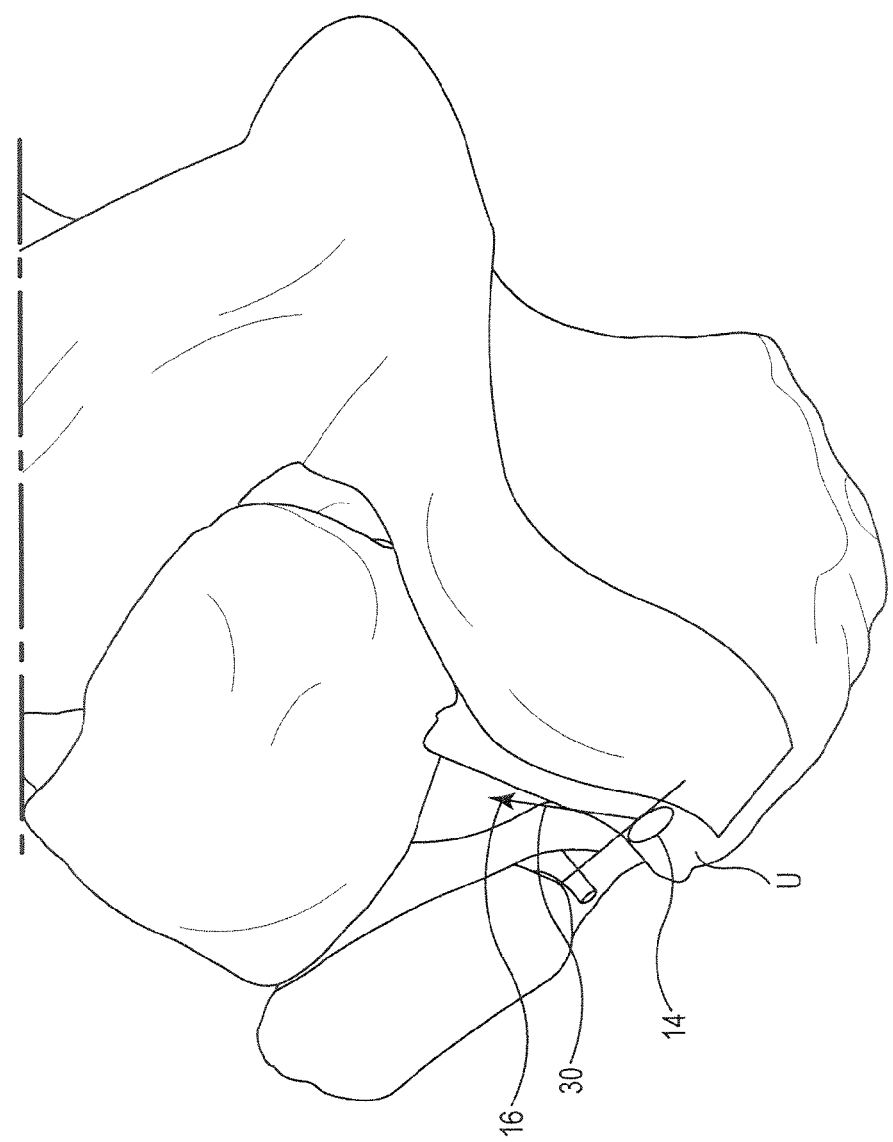
Figure 7:
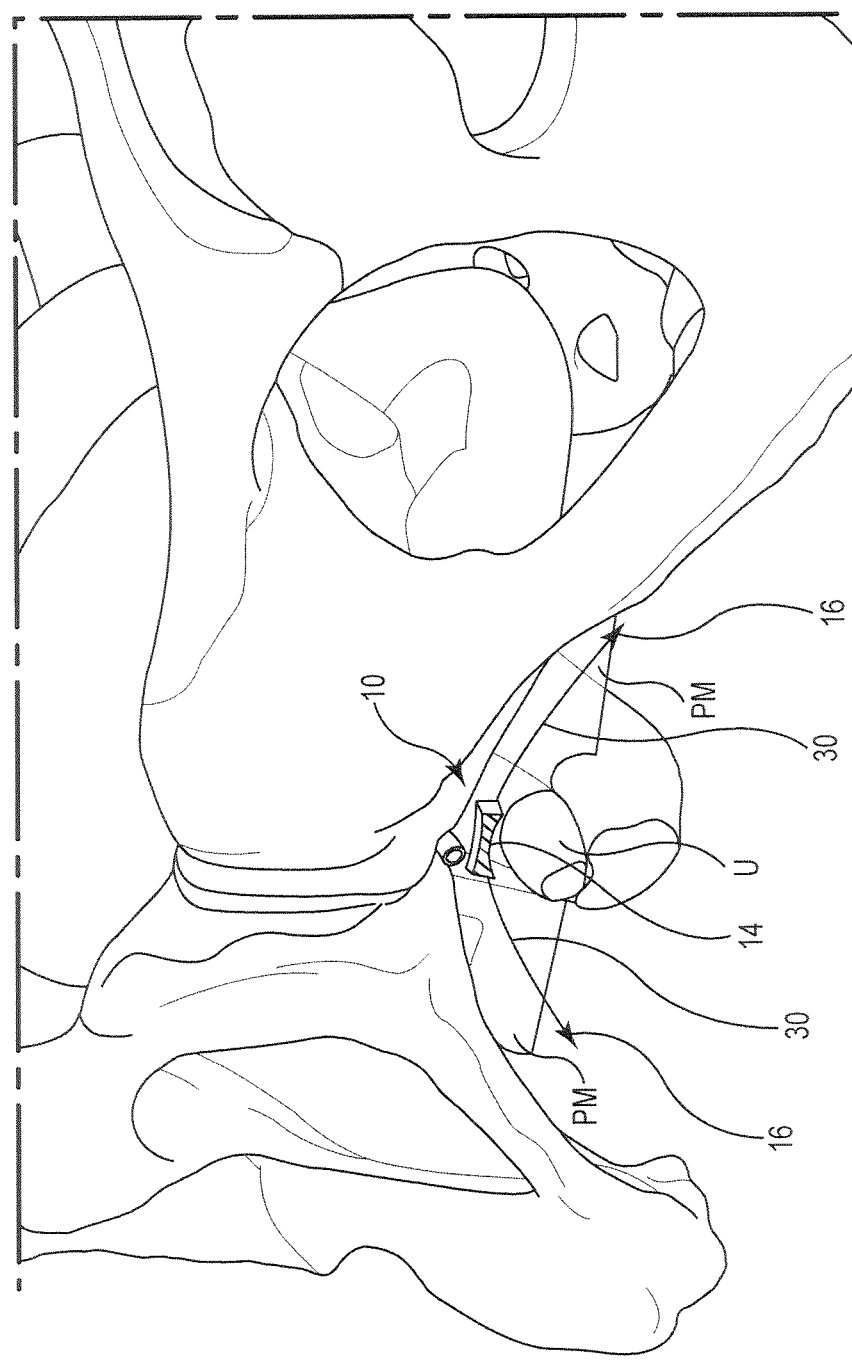
Figure 8:
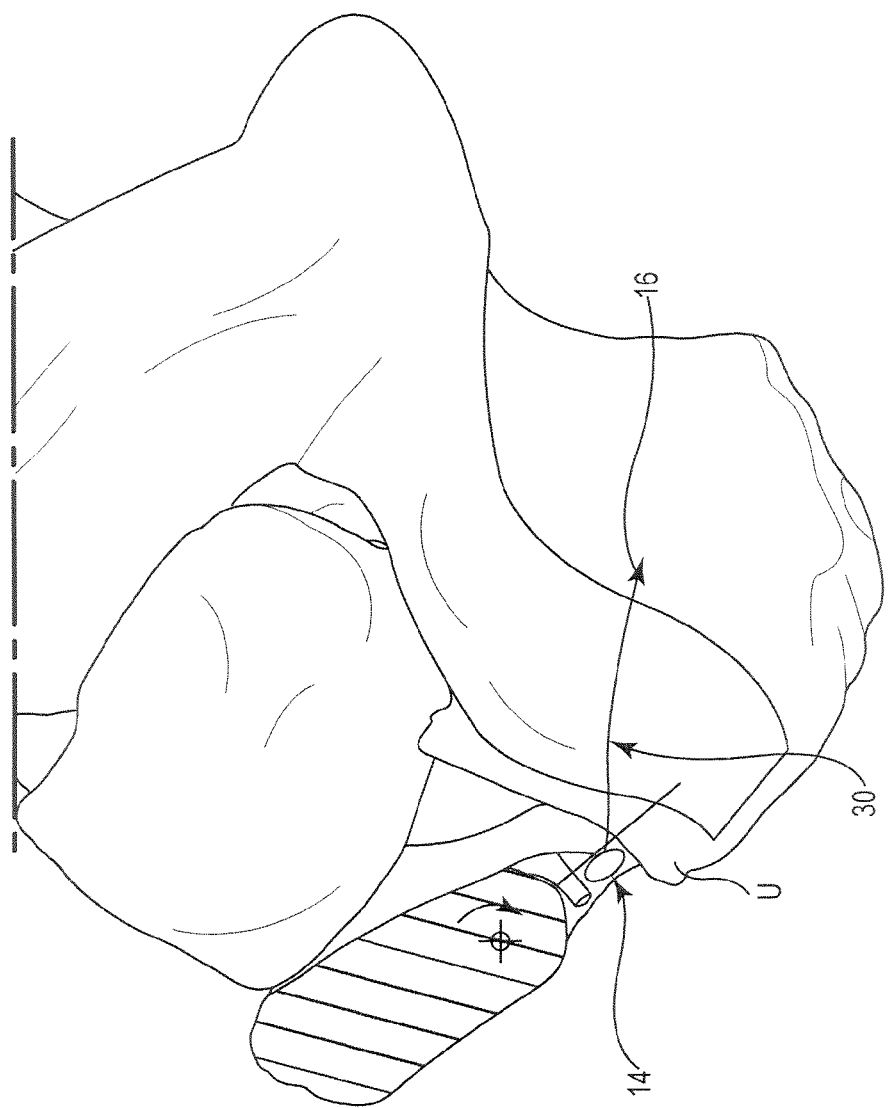
Figure 9:
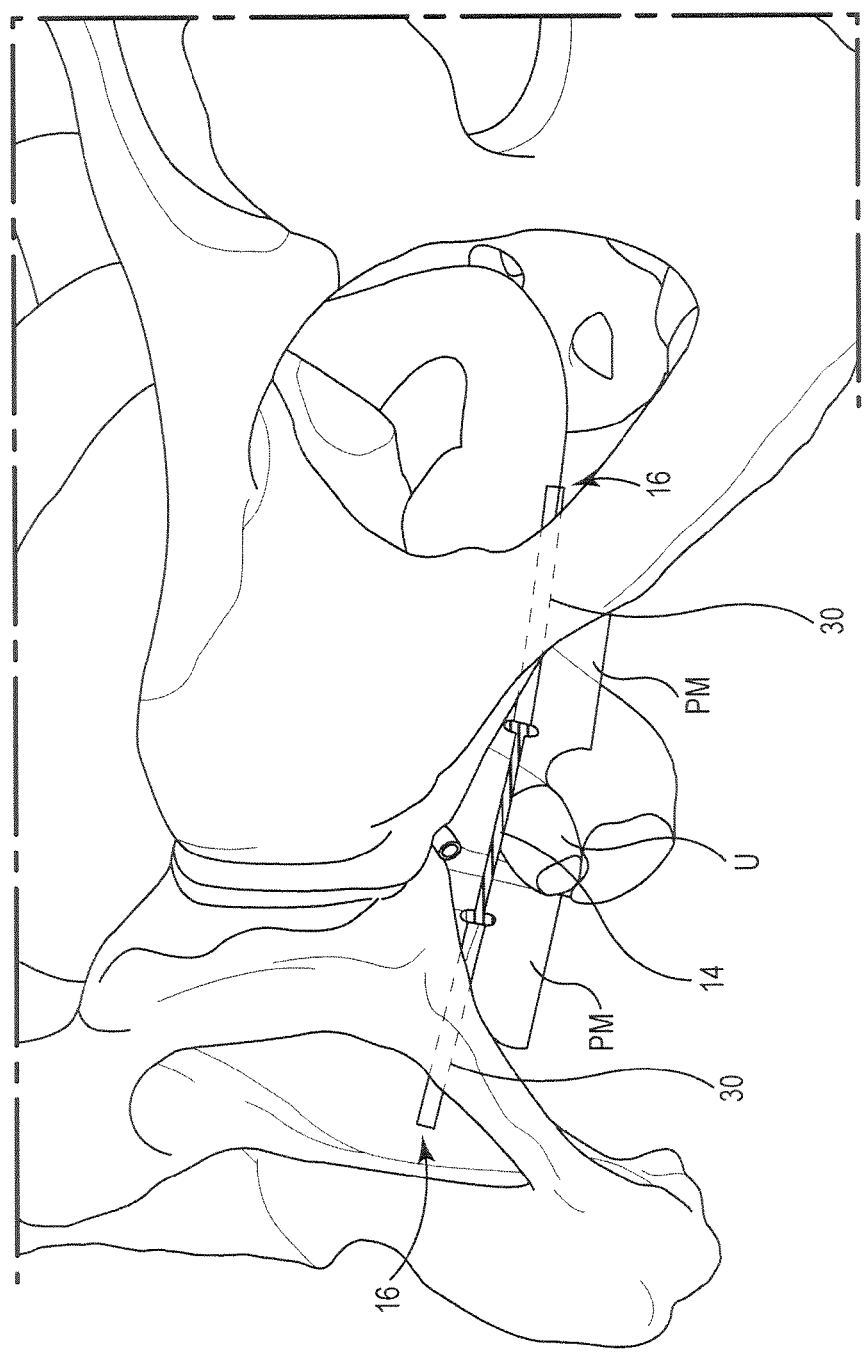

In other embodiments, as shown in FIGS. 3-8, the devices or anchors 16 may provide tension by insertion in various anatomical target sites. As depicted and described herein, the anchors 16 can be adapted to engage various tissue regions by using different positioning techniques. One anchoring location may be in the abdominal space or fascia by extending the extension member 30 through the retropubic cavity (FIGS. 3-4). Another anchoring location may be in the levator ani muscle or other inferior tissue, by threading the extension member 30 through the obturator foramen (FIGS. 6, 8-9). Alternatively, the anchors 16 may be anchored into the symphysis cartilage or pubic bone. In exemplary embodiments, the device 14 remains generally anterior to the urethra while the anchors 16 may be anchored in different membranes, proximal or distal the urethra U or perineal membrane PM. In still other example embodiments the device 14 may be positioned generally anterior of and lateral to the urethra U. Each positioning technique can provide effective urethral support and fixation to promote continence.

The embodiments of FIG. 9 illustrate an implant having a rigid or semi-rigid device 14 that can take either a straight or curved shape or path to provide the described support. As such, the implant 10 can vary in length and flexibility depending on the particular procedure and anatomical support application. For instance, the device 14 can be provided in a generally planar shape or bar configuration. The device 14 can be positioned proximate to the anterior portion of the perineal membrane PM and may extend forward towards or through the obturator foramen or like tissue distal the urethra U or corresponding support tissue. The placement or attachment of the device 14 proximate to the pelvis can prevent rotational movement. The rigid or semi-rigid device 14 can also be operatively coupled to anchoring members 16 to facilitate additional tissue fixation. Accordingly, the anchor 16 can be engaged into tissue laterally from the urethra U, towards or through the obturator foramen or like tissue target sites.

Figure 10:
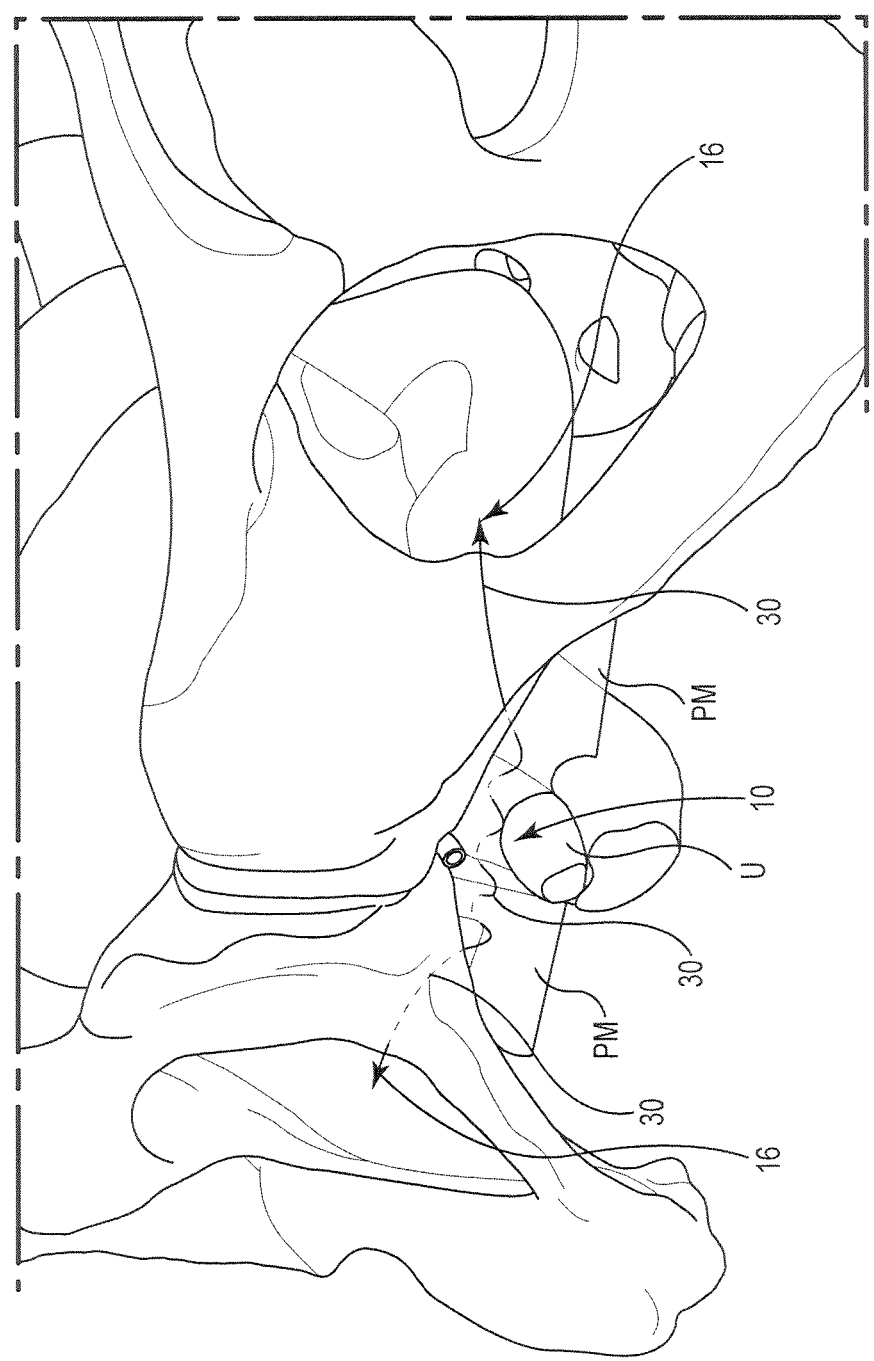
FIG. 10 is a schematic view of an extension member in undulating engagement with the perineal membrane, and distal anchoring a distance away from the perineal membrane, in accordance with embodiments of the present invention.

FIG. 10 shows a perspective view of an implant 10 utilized in an undulating fashion. The device 14 can be a sling, mesh, suture, or like member 30 stitched or weaved through, or in and out of, tissue such as the perineal membrane PM. The member 30 may be manufactured from biologic or synthetic mesh or other polymers, or a surgical suture material in various embodiments. This procedure and application of the implant 10 can create a restraint similar to the device 14 attached to a target tissue structure, e.g., the perineal membrane PM. Again, one or more anchors 16 can extend out laterally and engage the obturator foramen or like target tissue sites.

Figure 11:
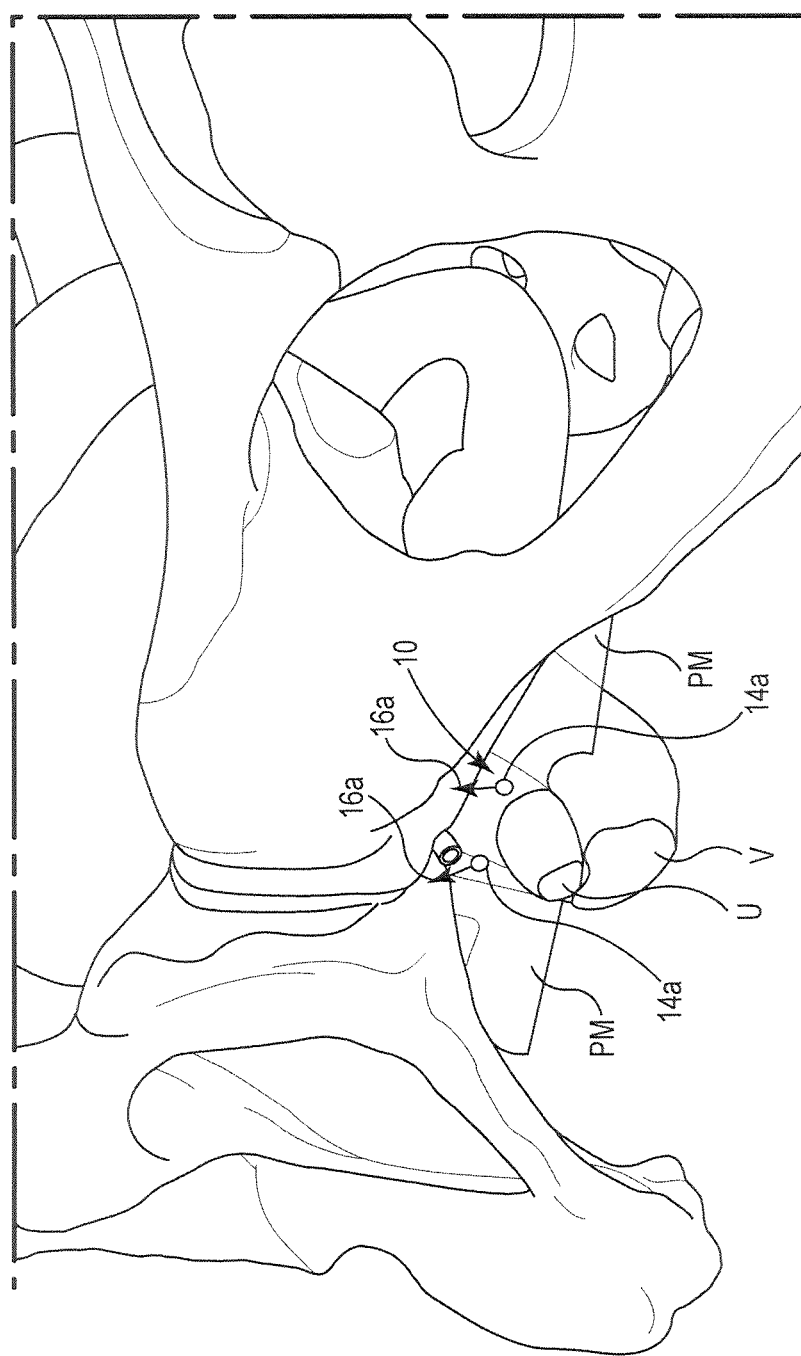

Turning now to FIG. 11, stitching, stapling or otherwise supporting the urethra U, or corresponding anatomical structures such as the perineal membrane PM, to a more superior structure can also be utilized to resist rotational motion of the urethra U or surrounding tissue. For example, stitching or stapling an inferior portion of the urethra U, or supporting tissue, to a more superior structure such as the pelvic symphysis can be utilized. In another embodiment, a first device 14a can be engaged or affixed in the inferior perineal membrane PM, and coupled to a second anchor 16a. The second anchor 16a can be anchored superiorly to the pelvic symphysis or other surrounding tissue. The member 30 can include a suture or other material. This procedure can be done on either side of the urethra U, or surrounding tissue, or above or below the urethra U or surrounding tissue. Stitching or stapling on the lateral perineal membrane PM can accomplish similar urethral fixation as described above.

As shown in FIG. 11a-11b, the one or more devices 14 can include extending anchor portions 94, 96 adapted to engage directly with the perineal membrane PM, or proximate the membrane. The device 14 can include a suture aperture 98, with one or more sutures 30 extending from the device 14 to one or more distal anchors 16. One or more suture locks 70, such as a one-way slider or like sliding or locking devices, can be slid along the free or trailing end of the one or more sutures 30 to affix or abut against the device 14 or tissue to fix the sutures 30 and the position of the device 14 in place once the desired tension and adjustment of the device 14 is established upon deployment and implantation.

The anchor portions 94, 96 can include one or more barbs, tines or like features to facilitate engagement of the device 14 with the perineal membrane PM or like tissue. Further, the one or more devices 14 of such embodiments can be positioned lateral to the urethra U, or above (supraurethral) or below (suburethral) the urethra U.

FIG. 12 shows yet another anchoring and/or supporting technique. One or more devices 14a can be anchored or engaged externally to the skin surface generally, or proximate or below the skin surface. The extension member 30 can extend superior through the pelvic cavity towards the bladder neck. The extension member 30 can be operatively coupled to the anchor or device 16a, which can be anchored or engaged with the perineal membrane PM or another appropriate tissue proximate or supporting the urethra U.

Figure 13:
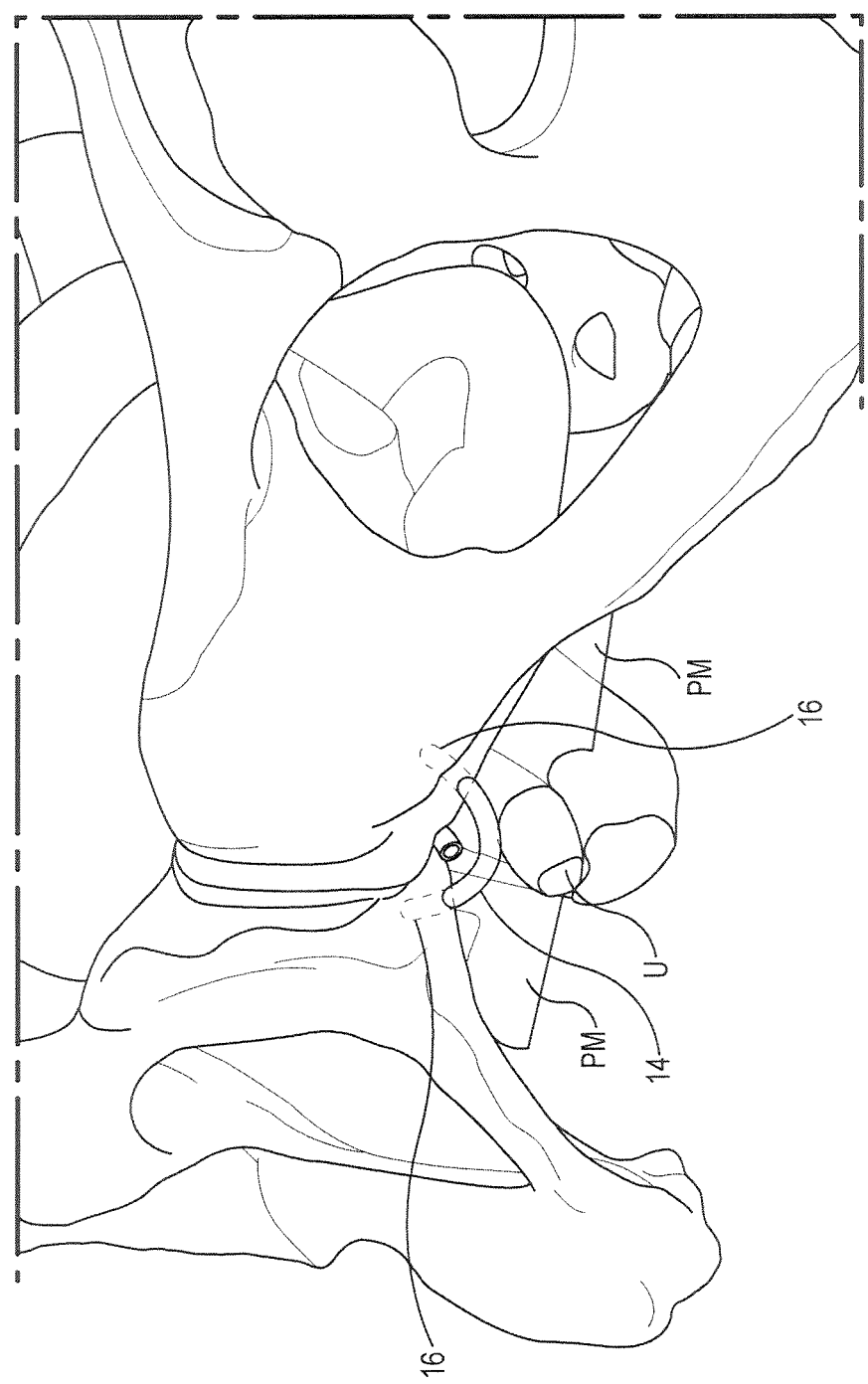
FIGS. 13-14 are schematic views of various shaped medial devices, in accordance with embodiments of the present invention.
Figure 14:
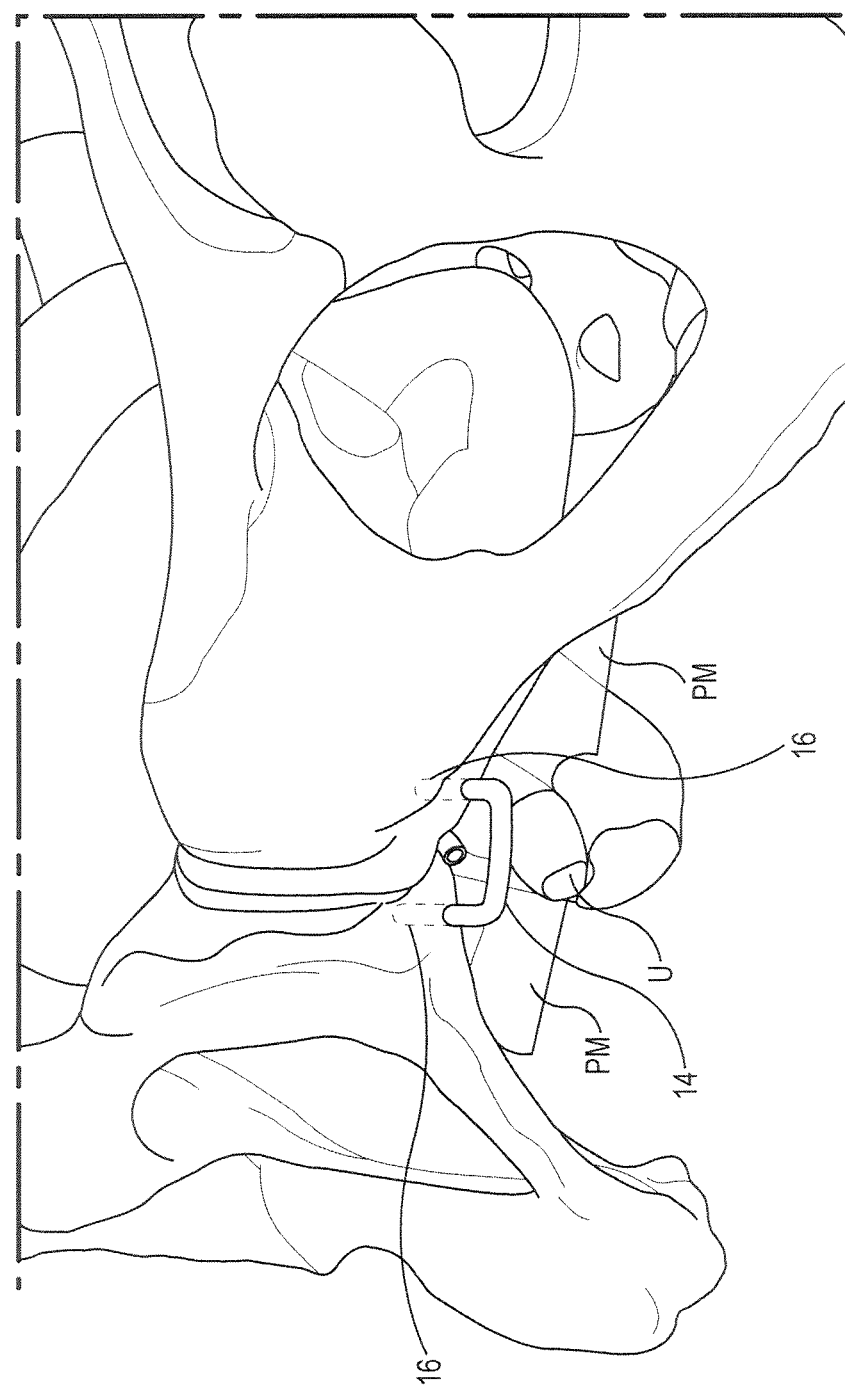
Figure 19A:
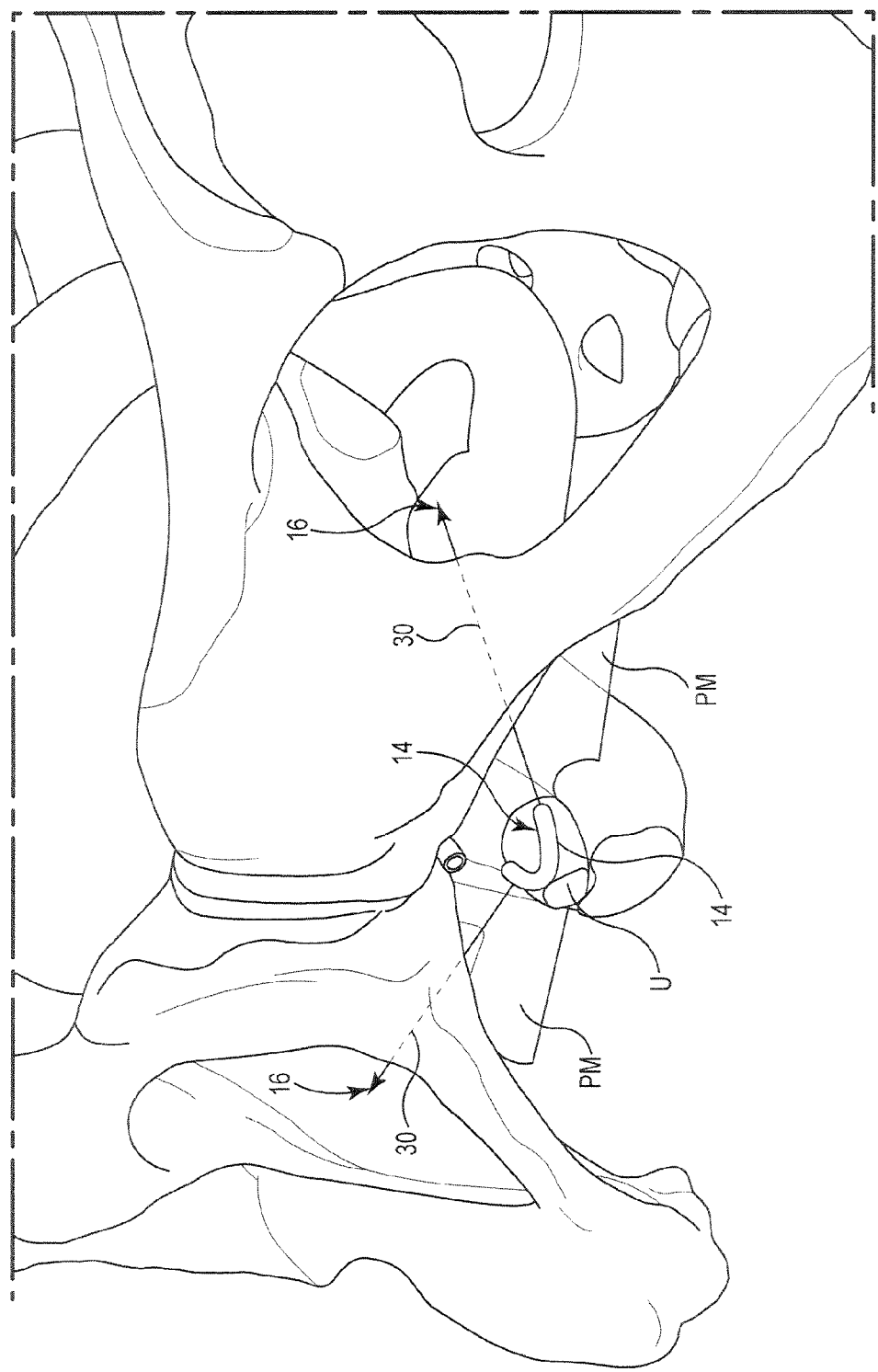
FIG. 19-19f is a schematic view of shaped medial devices adapted to surround at least a portion of the urethra or perineal membrane, and distal anchoring, in accordance with embodiments of the present invention.

FIGS. 13-14 depict a generally curved or angled flexible, rigid or semi-rigid device 14. This structure can be generally of a "V," "C" or "U" shape. The device 14 can be disposed proximate to or even abut the pelvic bone to oppose rotation of the urethra U as described herein. The device 14 can be operatively coupled to anchors 16 to provide for extra stability and fixation. The anchor 16 can be implanted or deployed into the pelvic symphysis or proximate tissue by means of a tool or anchoring mechanism or technique known to those skilled in the art. The device 14 can also be secured to resist lateral movement using the member 30 (e.g., suture), or another securing device, extending between the device 14 and the anchor 16.

FIGS. 15-16 depict a membrane-gathering device 14 for attachment to tissue, such as the perineal membrane PM. The device 14 can be provided next to the urethra U, e.g., above or below, and can include a wire 60 (e.g., polymer, metal, shape-memory construct, etc.). The wire 60 enters and re-enters through the perineal membrane, creating a loop-like structure (FIG. 15) to create tissue bunching or tension on the tissue (e.g., FIG. 16). When fully deployed, the loop device 14 plicates the membrane such that it stiffens or otherwise beneficially responds to intra-abdominal pressure different than what occurs with the rest of the membrane. This, in turn, changes the force vector for the tensioned site. The device 14 can be anchored via an anchor 16 or can be distinctly looped through the tissue to provide bunching tension during pressure events, such as abdominal pressure.

FIGS. 17-18 provides an embodiment adapted to promote suture buttressing or bridging of the perineal membrane PM. Namely, sutures 30, or like members or extensions, can be passed, e.g., percutaneously, laterally, across the perineal membrane PM and into the obturator muscles or like target tissue sites on both sides of the urethra U. One or more sutures 30 can be placed at the midline, or another anatomical site, with the sutures 30 drawn tight and brought together, or otherwise adjusted or tensioned, with a knot 62 or adapted device or mechanism to facilitate support of the perineal membrane PM. Under tension, the sutures 30 can provide a reinforcement of the membrane to limit motion and to support the urethra U. In certain embodiments, the members 30 can be anchored to the membrane with devices 14, while in others the members 30 can simply pass through or otherwise engage the corresponding membrane PM or like tissue, with stops, knots or like features 62 adapted to keep the members 30 attached to the perineal membrane to prevent unwanted sliding or traversal of the member 30 through the membrane once buttressing is achieved.

FIG. 19 shows a generally donut-shaped, circular or cylindrical device 14, such as a mesh or like construct, adapted for placement at or around the urethra U, e.g., at the perineal membrane PM, to provide a medial anchor and support device to spread or distribute the load around the urethra U. This can provide a long-term support with an overall reduction of local stress directly on the tissue or urethra U. The device 14 can be operatively connected to one or more anchors 16 via one or more members 30 such that the anchor 16 extends for fixation to the obturator membrane, abdominal fascia, rectus fascia, or like target tissue sites as described herein.

In other embodiments, the device 14 can partially shroud, cusp or otherwise grasp the perineal membrane PM, a portion of the urethra U, or tissue proximate the urethra U using a pre-formed device 14 material (e.g., mesh, polymer, or metal), or via an expanding frame construct. For instance, the device 14 can be constructed of an expandable frame that is collapsible during deployment and expands to provide a construct to cusp or otherwise grasp the tissue, such as the device 14 adapted to generally grasp on to a portion of the perineal membrane PM and/or the urethra U shown in FIG. 19a. The device 14 can be constructed of a material, such as a polymer or metal (e.g., Nitinol) having shape memory and/or living hinge structures to facilitate the selective expandability upon deployment. Again, one or more anchors 16 can be adapted to engage tissue away from the device 14 to facilitate support and tensioning for the implant 10, with the anchor 16 operatively connected to the device 14 via one or sutures or like members 30. As with any spanning, mesh, open or like embodiments of the device 14, openings or surface features can be included to promote tissue in-growth after deployment.

FIG. 19b-19f show embodiments of the implant 10 having a device 14 adapted to at least partially loop at or around the urethral opening in the plane of the perineal membrane PM to provide support for the urethra U. The devices 14 can include a base portion 90 and an anchoring portion 92. The base portion 90 can take on a myriad of shapes adapted to loop through or engage around tissue, e.g., v-shaped, semi-circular, circular, triangular, rectangular, and like shapes. The anchoring portion 92 can extend away from the base portion 90 and can include one or more barbs or tines adapted to facilitate fixation in soft tissue, cartilage or even bone. The devices 14 of these embodiments can be constructed at least in part of a generally rigid material, a semi-rigid material, or a flexible material, including various polymer or metal materials. FIGS. 19b-19c demonstrate this embodiment of the device 14 anchored into the pubic symphysis. Other anatomical target locations proximate or distal the perineal membrane PM are envisioned anchoring sites as well.

Figure 20:
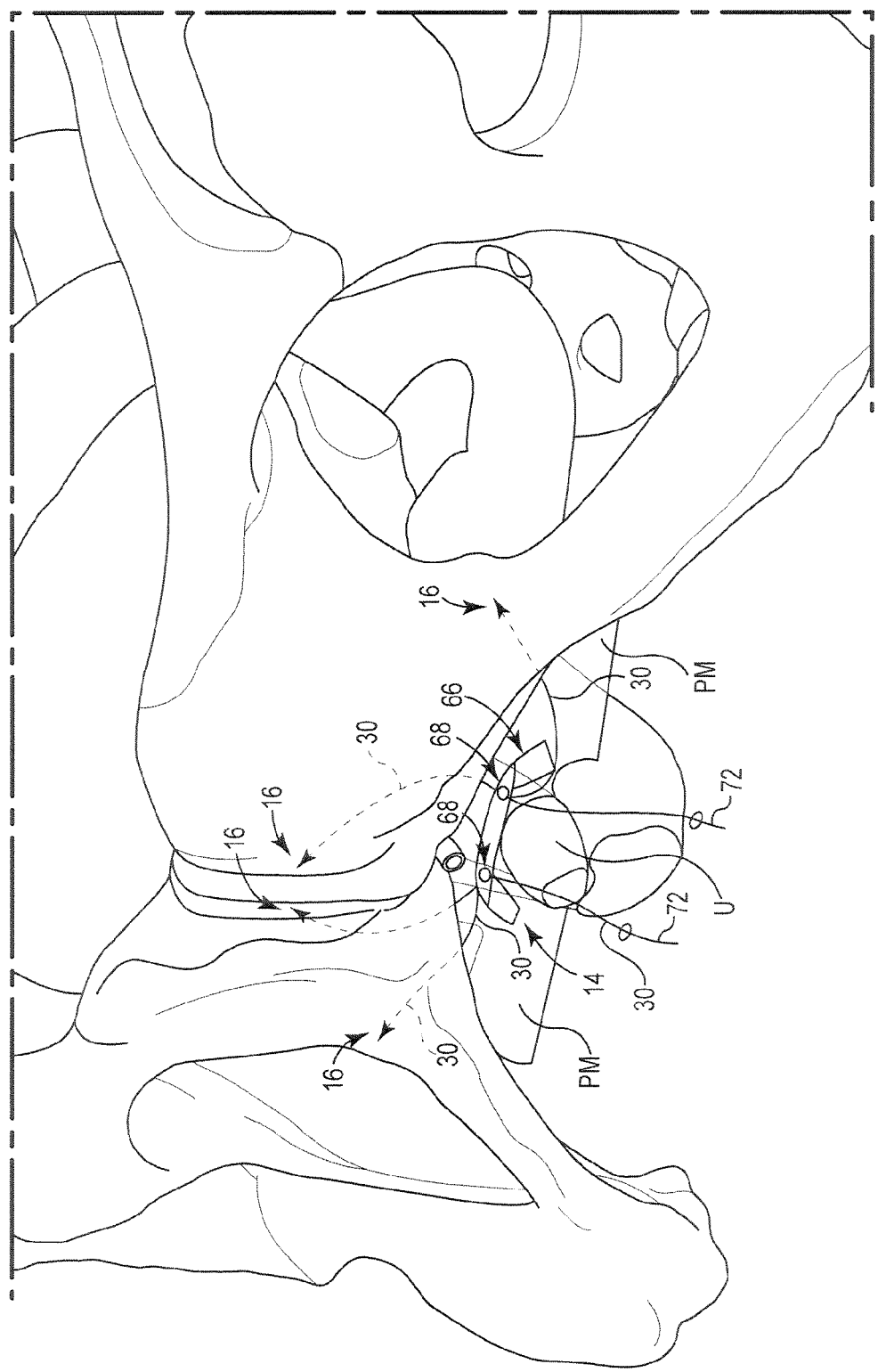
FIG. 20 is a schematic view of a medial device having a plate construct, and distal anchoring, in accordance with embodiments of the present invention.

FIG. 20 shows an embodiment of the implant 10 wherein the one or more devices 14 includes a plate-like device 66 adapted to generally position along and engage a portion of the perineal membrane PM (e.g., anterior). The device 66 can be constructed of various materials, e.g., generally flexible or rigid, and can include one or more connection features, such as apertures 68, adapted to receive or adjustably connect the one or more sutures 30 to the device 66. Various materials such as Kevlar, Gortex, dense woven mesh, sintered polymer (e.g., polyethylene terephthalate—PET) or like materials adaptable to conform or provide the disclosed shape and function of the device 66 can provide tissue adjustment, compression and/or support functions for the urethra U at the perineal membrane PM as disclosed herein. First anchor devices 16 can extend out laterally via the sutures 30, with second anchor devices 16 extending out or upward via sutures 30 to the pubic symphysis area (e.g., anchored on the posterior side) to provide tissue fixation, support and tensioning adjustment. One or more of the sutures 30 can be inserted through the apertures 68 and through the tissue of the perineal membrane PM such that a free end 72 of the sutures 30 extends out below or past the membrane. One or more suture locks 70, such as a one-way slider or like sliding or locking devices, can be slid along the free or trailing end 72 of the one or more sutures 30 to affix or abut against the device 66 or tissue to fix the sutures 30 and the position of the device 66 in place once the desired tension and adjustment of the device 66 is established upon deployment and implantation.

Figure 21:
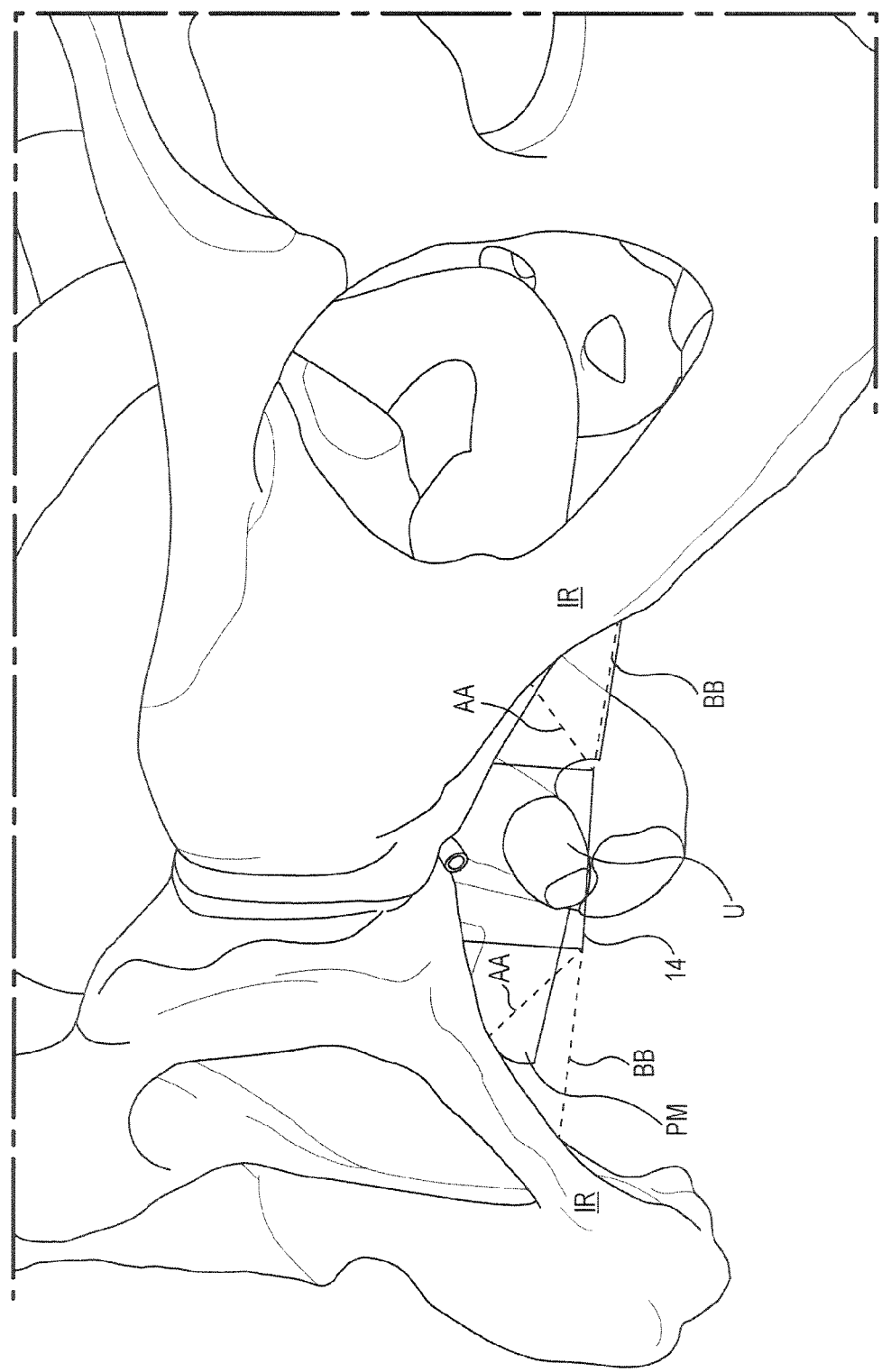
FIGS. 21-22 are schematic views of a various plate-like medial devices adapted to engage the perineal membrane above or below the urethra, in accordance with embodiments of the present invention.

FIG. 21 shows an embodiment having an implant device 14 adapted for deployment between the vagina and the urethra, e.g., at or along the perineal membrane PM. The device 14 can be constructed of mesh, polymer, metal or like materials. The device 14 can be generally U, C or like-shaped, and generally flexible or adjustable, with the device 14 anchored to the pubic symphysis or other tissue structures via anchors 16 or other engagement devices. In other embodiments, as shown in dashed lines AA, the device 14, or a portion thereof, can be manipulated or adjusted to angle out for anchoring to the ischiopubic ramus IR. In still other embodiments, as shown with dashed lines BB, the device 14, or a portion thereof, can extend generally straight across for anchoring to the ischiopubic ramus IR. Various bone anchors, sutures and like constructs and structures can be included to facilitate the described anchoring and tensioning configuration when bone anchoring is requires. In other embodiments, the device 14 can be anchored to structures other than bone, e.g., soft tissue. The device 14 can provide interference between the ischiopubic ramus bones (or thicker opposing sections of the perineal membrane PM) to prevent movement outward—e.g., of the urethra—caused by tissue rotation.

Figure 22:
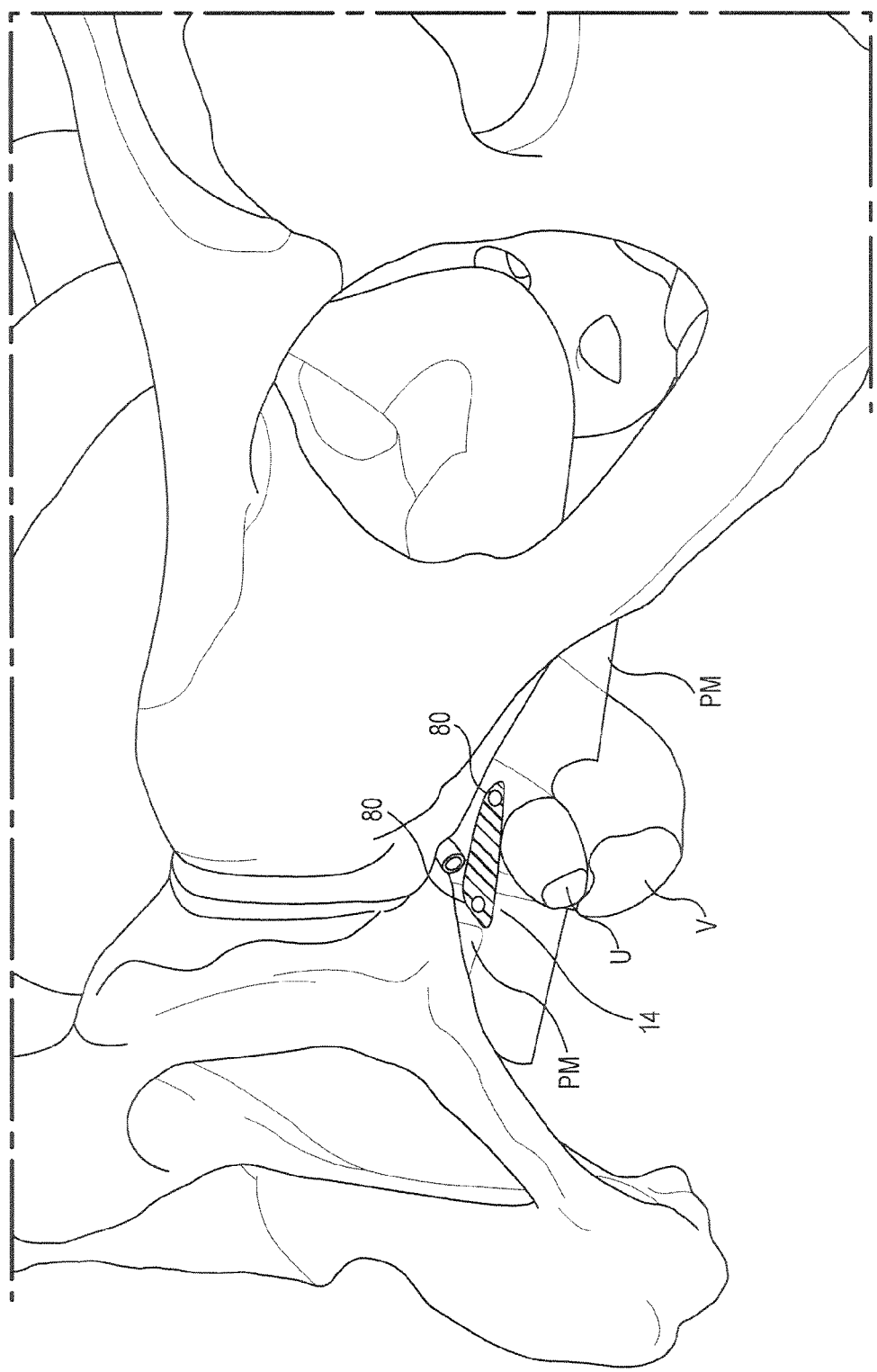
Figure 26:
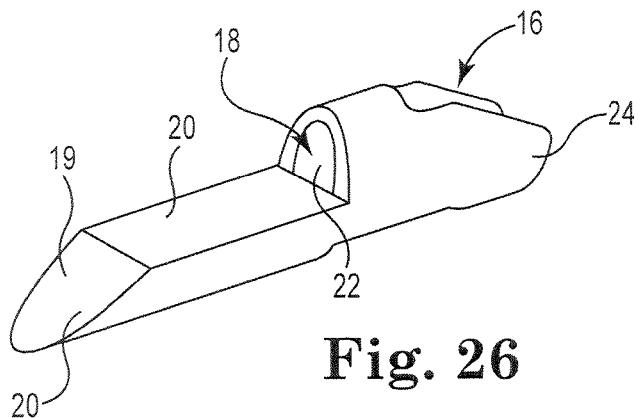
FIG. 26 is perspective view of a distal anchor device/barb, in accordance with embodiments of the present invention.
Figure 27:
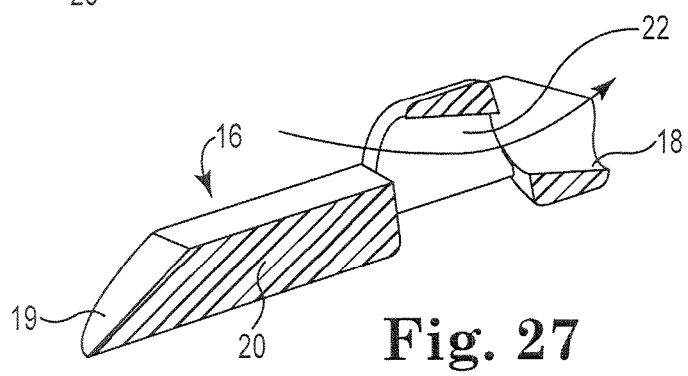
FIG. 27 is a partial sectional view of the distal anchor/barb of FIG. 26.
Figure 28:
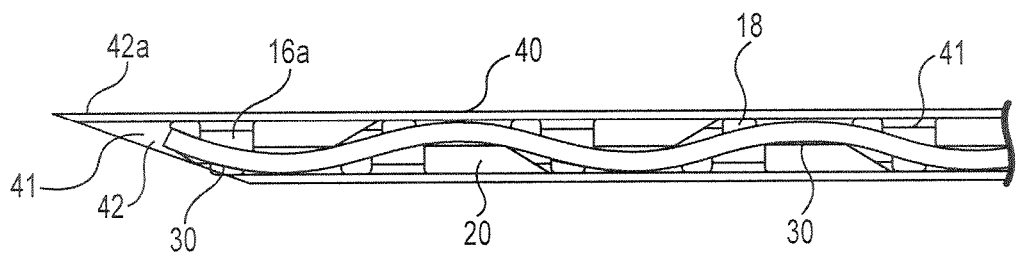
FIG. 28 is a side schematic view of a distal anchor array and suture within a delivery needle device, in accordance with embodiments of the present invention.

The embodiment of FIG. 22 can include a plate or semi-rigid, or semi-flexible, device 14 adapted for implantation in the area adjacent the urethral opening, generally in the plane of a portion of the perineal membrane PM. Deploying such a device 14 at this anatomical site can firm up the perineal membrane PM and create a structure to better resist interior pressure. The device 14 can include apertures 80 adapted to receive sutures 30, anchors or like members or devices for anchoring the device 14 to the membrane. Further, the device 14 can include a plurality of anchoring barbs, tines or like features to enable fixation at the implantation site, such as the perineal membrane PM. In certain embodiments, the device 14 can be collapsed, rolled up, or otherwise reduced in size to facilitate delivery and deployment to the target site, such as through or along a needle introduction tool. The device 14 can be constructed as a generally tubular stent-like structure or portion to provide the described and depicted means for attaching to and firming up the perineal membrane PM. While various embodiments disclose use of this device 14 as a strut-like perineal membrane PM support above the urethra U, the strut or perineal membrane reinforcement device 14 can also be disposed or anchored below the urethra U as well. Again, the plate or strut devices 14 can be directly anchored to the perineal membrane PM via sutures, or have members 30 extending out from the device 14 for anchoring at distal locations, such as the obturator foramen or other target sites described herein (e.g., via anchors 16).

FIGS. 23-24 show a T-support device 14. The device 14 can be placed in position via a small incision above or below the urethra U, with sutures or like members 30 passed through apertures 84 in the device 14. The device 14 can include a mechanism adapted to tighten down on the members 30 when desired tension is achieved and then a handle portion 86 can be removed to leave the members 30 and device 14 in place to reinforce or support the perineal membrane PM, and urethra U. Distal ends of the members 30 can include anchors 16 adapted to fixate within target tissue, such as the various targets sites disclosed herein.

In various embodiments, in addition to the devices 14 or as a separate treatment option, the perineal membrane PM tissue can be treated with cryoblation, or like techniques. For instance, a cryoprobe or like device can be inserted into the perineal membrane PM to shrink the tissue, thereby reducing any looseness in the tissue to promote strength and support of the urethra U. Various systems, devices, structures, techniques and methods, alone or in combination, as disclosed in U.S. Pat. No. 7,315,762 and U.S. Patent Publication Nos. 2008/0027422 and 2008/0027419, can be employed with the present invention to facilitate this treatment technique for the perineal membrane PM are, therefore, fully incorporated herein by reference in their entireties. Various energy sources, such as RF, can also be implemented to treat the target tissue. Other techniques can include the injection of a fast-curing polymer material that binds up upon curing within the body tissue, such as the perineal membrane PM, to provide a stronger target anchoring spot, or to simply tighten the tissue to promote continence.

Various embodiments of the distal anchor device 16 are envisioned for use with the present invention to promote tissue fixation of the implant 10 a distance away from the devices 14. For instance, as shown in FIG. 25 certain embodiments can include an anchor 16 having one or more barbs 90 to facilitate engagement with soft tissue, or even bone. Again, each anchor 16 can be operatively connected to the device 14 or perineal membrane PM via the one or more members 30, e.g., sutures.

Referring generally to FIGS. 26-34, the distal anchor devices 16 can include a body portion 18, one or more expandable barbs 20, a thru-aperture 22, and an opposing end 24. The suture 30 or like member is adapted to string or thread through the respective apertures 22 of a series or array 16n of such anchors to define the general elongate and expandable configuration shown. The array of anchors 16n can be inserted within and along the interior lumen 41 of a needle 40, cannula or like inserter or delivery tool.

In various embodiments, the lateral anchor devices 16 can be directed for engagement with tissue distal the device 14 at target sites such as the obturator foramen, obturator internus muscle, sacrospinous ligament, prepubic fascia or muscle, abdominal fascia, rectus fascia, puboprostatic ligament, the tendinous arch of the levator ani, the Cooper's ligament, and the pubic symphysis. Other distal target tissue sites for the anchors 16 capable of permitting tensioning support for the perineal membrane or other urethra-supporting tissue is envisioned as well. Unlike conventional sling device and implantation methods, the path from the perineal membrane to the distal anchor 16 of the present invention can follow a generally straight line into the obturator internus muscle, or like distal tissue.

Figure 29:
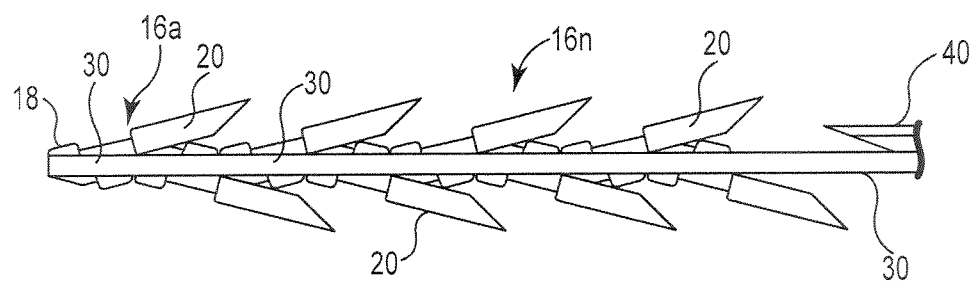
FIG. 29 is a side view of a distal anchor array and suture deployed from a delivery needle device, in accordance with embodiments of the present invention.
Figure 31:
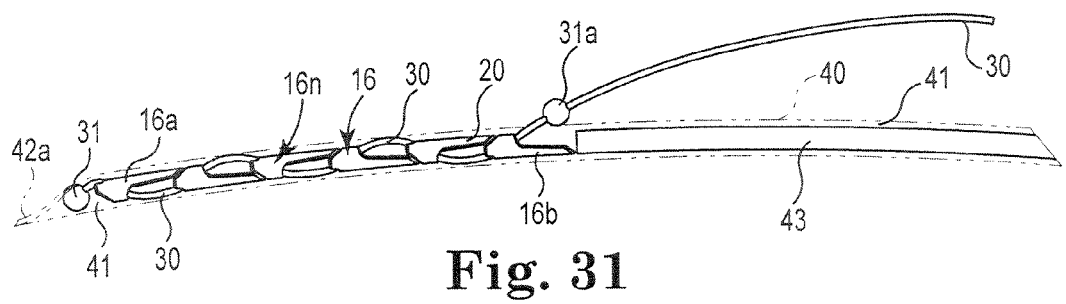
FIG. 31 is a side schematic view of a distal anchor array and suture within a slotted needle device, in accordance with embodiments of the present invention.
Figure 32:
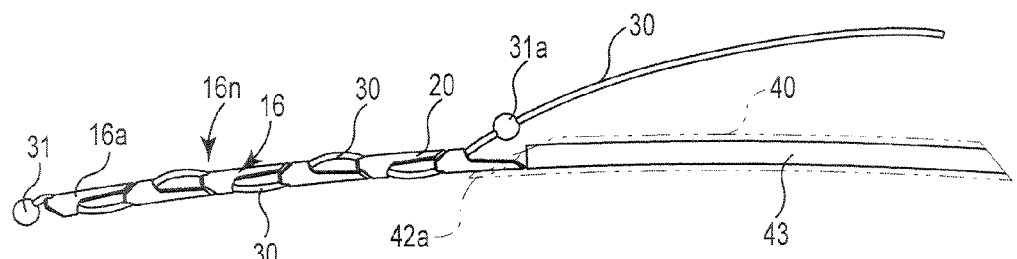
FIG. 32 is a side view of a distal anchor array and suture deployed from a slotted needle device, in accordance with embodiments of the present invention.
Figure 33:
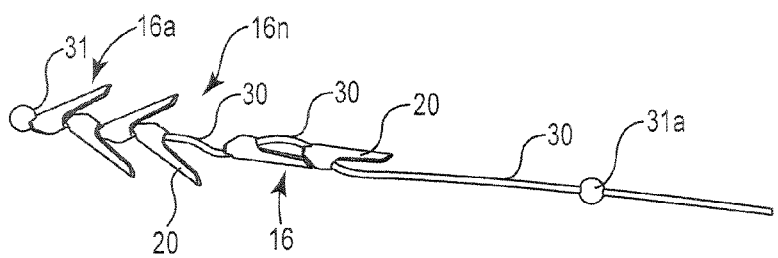
FIG. 33 is a side view of a distal anchor array and suture at least partially tensioned, in accordance with embodiments of the present invention.
Figure 34:
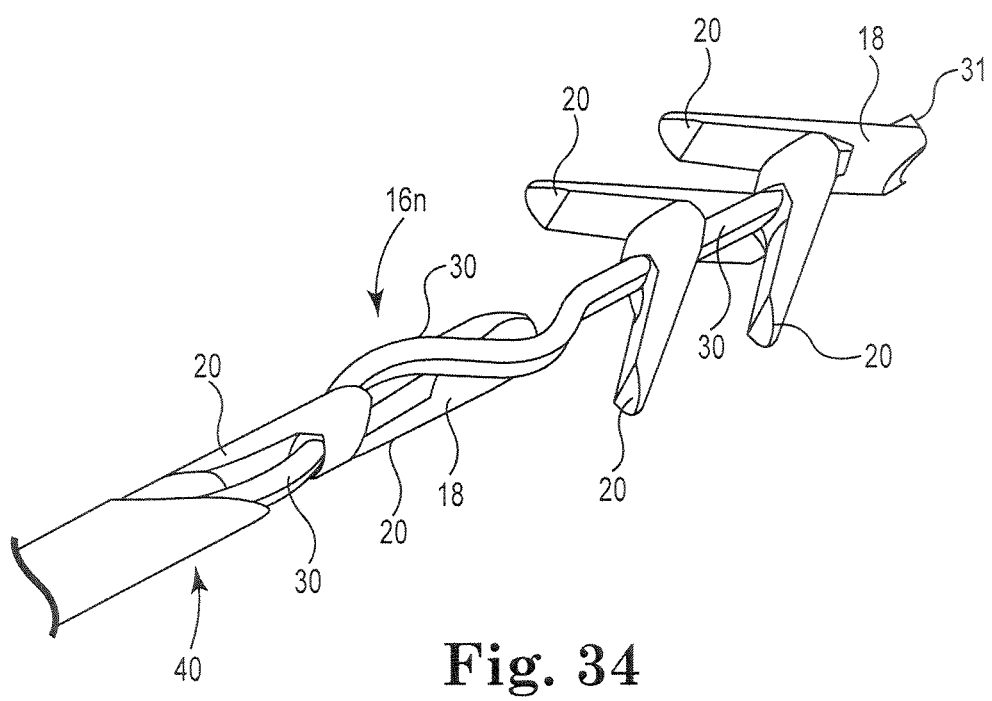
FIG. 34 is a perspective view of a distal anchor array and dual suture, in accordance with embodiments of the present invention.

Referring generally to FIGS. 28, and 30-32, the needle 40 can include an exit or opening 42 at a needle tip 42a. A series of anchors 16, such as the anchor array 16n, can include a lead anchor 16a adapted to first exit through the opening 42 upon deployment. In certain embodiments, the suture 30 path is generally undulating while within the needle 40, and even upon initial departure from the needle 40 (FIGS. 31-32), while it is generally brought into a straight or taut state upon full deployment from the needle 40 (FIGS. 29, 33-34). The end portion 24 of the lead anchor 16a can be permanently attached to the end of the suture 30 via bonding, adhesive, welding, knotting, or the like. The anchor 16 or its respective components can be molded together or otherwise attached to create the construct depicted and disclosed.

Each successive anchor 16, e.g., after lead anchor 16a, is alternately arranged such that they can be closely aligned along or within the lumen 41 of the delivery needle 40. The suture 30 passes through these anchors 16, and the anchors 16 can be adapted to slide on the suture 30. Again, when the anchor array 16n is inside the needle 40, the suture 30 can follow a serpentine or otherwise undulating path. A pusher rod 43, or like mechanism or device may be biased or pushed against the proximate anchor 16b (e.g., opposite end from the lead anchor 16a), as illustrated in FIGS. 31-32, such that the array of anchors 16n pushes against the distal end, or lead anchor 16a, that is fixed to the suture 30. This can help maintain the close alignment of the anchors 16 while inside the lumen 41 of the needle 40 and thus facilitate deployment.

When the delivery needle 40 is at the intended anchor position or target tissue, the array 16n can be deployed in various ways. In one method, the pusher 43 simply forces the anchors 16n out of the lumen of the needle 40. Some suture 30 tension can be maintained so that the anchors 16n are efficiently driven out in a straight line or path. In another method, the position of the anchors 16n relative to the tissue remains fixed or stationary (e.g., with the aid of the pusher 43) while the needle 40 is retracted back or away (e.g., slid) from the array 16n such that the anchors 16 are deployed from the lumen 41. With either approach, after the array of anchors 16n is completely outside the needle 40, tension can be applied against or upon the suture 30. This forces the individual anchors 16 to slide together and tilt outward at an angle relative to the suture while they embed into the tissue, creating firm engagement. The tilt angle, relative to a straightened suture, ensures engagement into tissue and is preferably 25 to 45 degrees. The pusher rod or member 43 can be a wire or tube that fits inside and through the proximal end of the needle 40, through the lumen 41, and acts against at least one of the anchors, directly or indirectly, including the most proximal anchor.

In certain embodiments, the devices 14 or 16, can be fabricated using a metal injection molding process, or from a molded resin material (e.g., 720FC resin, polycarbonate, PEEK, nylon), with an exemplary Prolene monofilament, or braided, suture 30 threaded therethrough. The anchors 16 can be easily inserted through the lumen 41 of the needle 40 and arranged in an alternating pattern—e.g., angular orientation pattern—along the suture 30. For instance, the alternating angular pattern of the anchors 16 in FIGS. 33-34 are approximately 180 degrees, whereas other alternating angular patterns for the anchors 16 in the array 16n can be approximately 90 degrees. Of course, a myriad of alternate angular patterns and orientations are envisioned for embodiments of the invention depending on the particular deployment, anchoring and engagement needs. The suture 30 can be lightly tensioned to bring all the anchors 16 in the array 16n together while holding the pusher 43 in place. Again, while holding the pusher 43 stationary, the needle or cannula 40 can be retracted, leaving the array 16n, and the respective anchor barbs 20 embedded in tissue. A slight tug of the suture 30 can bring the anchors together and take up any initial slack in the suture line 30.

Embodiments of the tissue anchoring devices and methods can include a reduced trauma explantation (e.g., removal from tissue) configuration and mechanism for the barbed soft tissue anchors, e.g., the anchors 16, described and depicted herein. For instance, one solution is to attach an explantation tether to the leading anchor 16a of the array 16n. This could be in the form of a separate suture, or continuation of the existing traction suture 30 that leads back out of the implantation path. To remove the anchor 16, or anchor array 16n, the physician simply pulls on this tether, causing the anchor 16 to double-back on itself and pull out atraumatically—e.g., through the defined tissue path or tissue penetration site. This could be done during the initial implantation procedure or at a later time in the event that the device 16, or implant 10, must be disengaged or removed.

The anchor array 16n is thread or otherwise provided along the suture 30, or paired sutures 30 (e.g., FIG. 34), and can be delivered via a percutaneous passage inside a hypotube or the needle 40. This allows for controlled delivery of the anchor array 16n such that the needle tip 42a can be selectively repositioned before the anchors are set in soft tissue.

Figure 30:
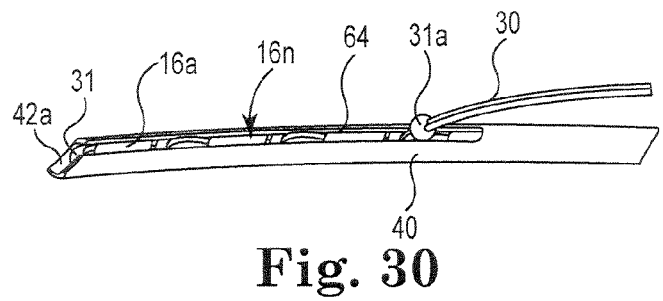
FIG. 30 is a perspective view of a distal anchor array and suture within a slotted needle device, in accordance with embodiments of the present invention.

Referring generally to FIGS. 30-32, embodiments of the needle system 40 can include a slotted needle configuration, with the needle 40 including a slot or groove 64 along a distal or end portion of the needle 40 body such that a portion of the suture 30 can pass outside the lumen 41 of the needle 40 during deployment. The slot 64 can be created in or along a portion of the needle 40 by milling, laser cutting, EDM machining, or using other similar fabrication, manufacturing or formation methods. For needles 40 requiring some curvature to facilitate use and deployment, the slot machining may be done before or after the bending operation for the needle 40. With a curved needle 40, the slot 64 can be on the outer side of the bend. This, in turn, can promote keeping the portion of the suture 30 that lies in the slot 64 to stay inside the lumen 41 when under tension.

As described, a pair of sutures 30, e.g., FIG. 34, can pass through each anchor 16 in the array 16n, and follow a serpentine or undulating path within the needle 40. A knot, bead, stop, member or like structure 31 at the distal end of the suture 30 proximate or in front of the leading anchor 16a can act as a stop for the lead anchor 16a. A second knot, bead, stop, member or like structure 31a, can be included at a portion of the suture 30, or paired suture, near the most proximal anchor 16b, and/or outside the slot 64 (e.g., FIG. 30).

Further, embodiments of the needle 40 including the slot 64 configuration can facilitate easier and more efficient use and deployment of the medial device 14. The medial device 14 can be attached to, or threaded or provided along a portion of the suture 30 that does not need to be constrained or fit within the relatively thin and small needle 40 or lumen 41. As such, the slot 64 provides a length of suture 30 that can ride outside of the lumen 41, with the medial device 14 attached or provided along that external length of suture 30. This provides greater flexibility for the design and construct of the medial anchor device and the respective delivery method. In addition, the pusher 43 will not interfere (e.g., traverse alongside) with the proximal length of the suture 30 provided before the anchor array 16n, as the proximal portion of the needle lumen 41 will be free of the suture 30.

The proximal stop 31a can also be used to keep the anchor barbs 20 from spreading apart during assembly and during the deployment of the anchors 16n. With the slotted needle 40, the knot, bead or stop 31a can be positioned either inside or outside the lumen 41. One advantage for positioning the stop 31a outside is that it can introduce enough drag to enable retraction of the needle 40 while still keeping the anchors 16 in place. In certain embodiments, this can preclude the need for an internal pusher 43 to hold the anchors 16 in place upon deployment. The stop 31a could take on nearly any size or shape, and material. Also, the anchor system can include intermediate knots, beads or stops 31 that separate smaller or distinct groupings of anchors 16.

Portions of the distal anchors 16, and the device 14, can include self-expanding structures or materials such that the devices 14, 16 can be generally collapsed or reduced in sized during deployment, with or without a needle device 40, and expanded after penetration in the target tissue site to provide desired tissue engagement. Certain devices 14, 16 can include one or more shape memory portions, or living hinges, to facilitate this structural self-expansion upon deployment and tissue engagement. Further, embodiments of the devices 14, 16, can include helical portions, threaded portions, hooks, clips, flexible barbs, textured surfaces, and like members or structures to promote tissue engagement.

The support or extension members 30 can apply mechanical traction to the urethra in a manner similar to a mini-sling device. However, a benefit of embodiments of the present invention is that the transvaginal placement of the structures and devices does not leave exposed material (e.g., implant mesh) inside the vaginal cavity. For example, the implanted device 10 position is generally blind and lies beyond the superficial mucosal layer of the vaginal wall. Reducing or eliminating the exposed material minimizes the risk of infection, irritation at the surface of the vaginal wall, and provides cosmetic improvement and reduces interference with sexual activity.

The medial or proximal device 14 can include a "toggle" anchor, which is a small, elongated structure that can be placed through a small puncture or like incision and then rotates after deployment so that it cannot back out through the incision hole. Other anchoring devices and methods can be employed with the present invention as well.

As shown with various embodiments, the suture 30 can weave or thread in and out of, and along, the tissue, e.g., the perineal membrane above or below the urethra U, to provide a supportive undulating layout for the suture 30 and device 14 combination. This can facilitate attachment, better distribute pulling force on or along the tissue, and provide like support benefits.

Again, the one or more distal anchors 16 can be placed in a lateral or superior position such that a connection (e.g., suture 30 or wire connection) between the medial and lateral devices 14, 16 can provide tensile support for the urethra during stress events. The anchor device 16 can be fixated to, or engaged with, the obturator membrane, obturator internus, tendinous arch of the levator ani (white line), the Cooper's ligament, sacrospinous ligament, prepubic fascia or muscle, the pubic symphysis cartilage, abdominal fascia, or other stable anatomical features.

Various procedural steps or methods can be employed to deploy the implant 10 of the present invention. In one embodiment, the medial device 14 is implanted, a needle is withdrawn, a free suture or connector end is delivered through the insertion opening, the lateral (e.g., obturator) anchor 16 is delivered and implanted, and the connecting suture 30 is properly tensioned between the devices 14, 16 to provide proper support.

In certain circumstances, it may be desirous to provide pre-loaded tension options for one or more of the devices 14, 16. Preloading can be achieved by pretensioning the suture 30 during the implantation procedure or could be achieved by creating mechanical pretension internally in the devices 14, 16, or mechanisms operatively connected to the devices 14, 16. As such, a constant rest load against tissue (which might stretch) can be provided.

In use, a patient can be placed in a lithotomy position for the implantation procedure. A physician may make one or more incisions through the perineal tissue above or below the urethra of the patient. Alternatively, the physician may make one or more vaginal incisions to access the tissue superior to the urethra. The physician may use the needle delivery device 40 to implant the devices or anchors. The medial or proximal device 14 can then be implanted through the perineal incision, thereby reducing the invasiveness of the procedure. The delivery device 40 may be configured to allow insertion through a single or multiple perineal or transvaginal incisions. In other embodiments of the implant treatment procedure, needle 40 can be directed "outside-in,"

from the skin through the obturator membrane, then with an device 14 engaged with the perineal membrane. Further, the devices 14 can include suture loops. The loops can be tied from the peritoneum side. From the obturator side, the multiple loops or sutures 30 can then be tied around the anchor for fixation.

In certain embodiments, as mentioned herein, it may be beneficial to modify the target anchor zone or site (e.g., perineal membrane) through the use of injectables such as a scarring agent, proteins, polymers, or other materials that significantly increase tissue strength in the region. After allowing this treatment to set up, the continence implant 10 can be implanted in a follow-up procedure.

The systems, devices, configurations and methods disclosed herein have generally described anchors that are symmetrically, bilaterally, positioned about the urethra. However, a single side deployment configuration can still achieve continence and is available with various embodiments. For instance, a single medial device 14 and lateral anchor 16, or lateral anchor array 16*n*, can be connected by a suture 30 to support and adjust the perineal membrane, above or below the urethra.

The systems, their various components, structures, features, materials and methods of the present invention may have a number of suitable configurations as shown above. Various methods and tools for introducing, deploying, anchoring and manipulating implants or to treat incontinence and prolapse as disclosed in the previously-incorporated references are envisioned for use with the present invention as well.

A variety of materials may be used to form portions or components of the implants and devices, including Nitinol, polymers, elastomers, porous mesh, thermoplastic elastomers, metals, ceramics, springs, wires, stent-like constructs, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A urethral support system for treating incontinence in a patient, comprising:
    an elongate first implant device having a first end and a second end, the first implant device having a first medial device having a medial width and provided at the first end of the first implant device and adapted to anchor into a portion of the perineal membrane above the urethra of the patient and not below the urethra, the first medial device having a first anchor portion, a second anchor portion, and an aperture disposed between the first anchor portion and the second anchor portion, the first implant device having a first suture configured to extend through the aperture, and a first distal anchor device provided at the second end of the first implant device and operatively connected to the first medial device via the first suture, at least the medial width of the first medial device being larger than a width of the first suture, the first distal anchor device adapted to engage tissue distal to the perineal membrane;
    an elongate second implant device, physically separate from and unconnected to the first implant device, having a first end and a second end, the second implant device having a second medial device provided at the first end of the second implant device and adapted to anchor into a portion of the perineal membrane above, and not below, the urethra of the patient spaced away from the first implant device, the second medial device having a first anchor portion, a second anchor portion, and an aperture disposed between the first anchor portion of the second medial device and the second anchor portion of the second medial device, the second implant device having a second suture configured to extend through the aperture of the second medial device, and a second distal anchor device provided at the second end of the second implant device and operatively connected to the second medial device via the second suture, the second distal anchor device adapted to engage tissue distal to the perineal membrane.

2. The system of claim 1, wherein the first distal anchor device includes a first array of anchors, each of the first array of anchors having expandable barbs.

3. The system of claim 1, wherein the first anchor portion of the first medial device includes one or more first barbs, and the second anchor portion of the first medial device includes one or more second barbs.

4. The system of claim 1, wherein the first distal anchor device of the first implant device is adapted to engage a target tissue site selected from the group consisting of: the obturator foramen, obturator internus, abdominal fascia, sacrospinous ligament, prepubic fascia, rectus fascia, the tendinous arch of the levator ani, the Cooper's ligament, and the pubic symphysis cartilage.

5. The system of claim 1, wherein the first medial device of the first implant device is a mesh device.

6. The system of claim 1, wherein the first medial device of the first implant device is a plate device.

7. The system of claim 1, wherein the first medial device of the first implant device is a toggle tissue anchor device.

8. The system of claim 1, wherein the first medial device of the first implant device is at least partially flexible.

9. The system of claim 1, wherein the first medial device of the first implant device is at least partially rigid.

10. A urethral support system for treating incontinence in a patient, comprising:
    an elongate first implant device having a first end and a second end, the first implant device having a first medial device provided at the first end of the first implant device and adapted to anchor into a portion of and span across a portion of the perineal membrane adjacent the urethra of the patient, the first medial device having a first anchor portion, a second anchor portion, and an aperture disposed between the first anchor portion and the second anchor portion, the first implant device having a first suture configured to extend through the aperture, the first suture having a first end portion and a second end portion, the first implant device including a first distal anchor device provided at the second end of the first implant device, the first distal anchor device being coupled to the first end portion of the first suture, the first distal anchor device adapted to engage tissue superior to the perineal membrane;

an elongate second implant device, not connected to and physically separate and spaced from the first implant device, having a first end and a second end, the second implant device having a second medial device provided at the first end of the second implant device and adapted to anchor into a portion of and span across a portion of the perineal membrane adjacent the urethra of the patient spaced away from the first implant device, the second medial device having a first anchor portion, a second anchor portion, and an aperture disposed between the first anchor portion of the second medial device and the second anchor portion of the second medial device, the second implant device having a second suture configured to extend through the aperture of the second medial device, the second suture having a first end portion and a second end portion, the second implant device including a distal anchor device provided at the second end of the second implant device, the second distal anchor device being coupled to the first end portion of the second suture, the second distal anchor device adapted to engage tissue superior to the perineal membrane.

11. The system of claim 10, wherein the second distal anchor device includes a first array of anchors, each of the first array of anchors having expandable barbs.

12. The system of claim 10, further including:
a first suture lock coupled to the second end portion of the first suture; and
a second suture lock coupled to the second end portion of the second suture.

13. The system of claim 10, wherein the first distal anchor device of the first implant device is adapted to engage a target tissue site selected from the group consisting of: the obturator foramen, obturator internus, abdominal fascia, sacrospinous ligament, prepubic fascia, rectus fascia, the tendinous arch of the levator ani, the Cooper's ligament, and the pubic symphysis cartilage.

\* \* \* \* \*